US012558405B2

(12) United States Patent
Jo et al.

(10) Patent No.: US 12,558,405 B2
(45) Date of Patent: Feb. 24, 2026

(54) PHARMACEUTICAL COMPOSITION USING ENDOGENOUS CELLS FOR PREVENTING OR TREATING MUSCULOSKELETAL DISORDERS

(71) Applicant: SEOUL NATIONAL UNIVERSITY R&DB FOUNDATION, Seoul (KR)

(72) Inventors: Hyun Chul Jo, Seoul (KR); Seung Yeon Lee, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 920 days.

(21) Appl. No.: 17/422,266

(22) PCT Filed: Oct. 22, 2019

(86) PCT No.: PCT/KR2019/013906
§ 371 (c)(1),
(2) Date: Jul. 12, 2021

(87) PCT Pub. No.: WO2020/145491
PCT Pub. Date: Jul. 16, 2020

(65) Prior Publication Data
US 2022/0088153 A1 Mar. 24, 2022

(30) Foreign Application Priority Data
Jan. 11, 2019 (KR) ........................ 10-2019-0003742

(51) Int. Cl.
| | |
|---|---|
| *A61K 38/48* | (2006.01) |
| *A61K 31/196* | (2006.01) |
| *A61K 33/06* | (2006.01) |
| *A61K 35/16* | (2015.01) |
| *A61K 35/19* | (2015.01) |
| *A61P 19/04* | (2006.01) |
| *A61P 19/08* | (2006.01) |

(52) U.S. Cl.
CPC .......... *A61K 38/482* (2013.01); *A61K 31/196* (2013.01); *A61K 33/06* (2013.01); *A61K 35/16* (2013.01); *A61K 35/19* (2013.01); *A61P 19/04* (2018.01); *A61P 19/08* (2018.01)

(58) Field of Classification Search
CPC ......... A61K 38/482; A61P 19/04; A61P 19/08
See application file for complete search history.

(56) References Cited

U.S. PATENT DOCUMENTS

| | | | | |
|---|---|---|---|---|
| 11,458,166 B2 * | 10/2022 | Bastianelli | ......... | A61K 31/4168 |
| 2017/0080028 A1 * | 3/2017 | Turzi | .................. | A61L 26/0042 |

FOREIGN PATENT DOCUMENTS

| | | | | |
|---|---|---|---|---|
| KR | 101038616 | 5/2011 | | |
| KR | 1020130133612 | 12/2013 | | |
| WO | WO-2004024198 A1 * | 3/2004 | ............. | A61K 35/58 |

OTHER PUBLICATIONS

Matteo et al. 2015 (Musculoskelet Surg. Apr. 2015;99(1):1-9. doi: 10.1007/s12306-014-0340-1) (Year: 2015).*
Salamanna et al (Biomed Res Int. 2015:2015:846045 (Year: 2015).*
Nazaroff et al. 2021 (PLoS One. Apr. 23, 2021;16(4): e0250007. doi: 10.1371/journal.pone.0250007) (Year: 2021).*
Jamal et al. 2022 (J Clin Orthop Trauma. Feb. 2022; 25: 101759. Published online Jan. 4, 2022. doi: 10.1016/j.jcot.2021.101759) (Year: 2022).*
Bacevich et al. 2024 (Biologics . Jan. 25, 2024:18:29-59. doi: 10.2147/BTT.S290341. eCollection 2024) (Year: 2024).*
Marra et al. (Joints. Oct.-Dec. 2016; 4(4): 202-213) (Year: 2016).*
Salamanna, F., et al., "New and Emerging Strategies in Platelet-Rich Plasma Application in Musculoskeletal Regenerative Procedures: General Overview on Still Open Questions and Outlook," BioMed Research International, vol. 2015, Article ID 846045, pp. 1-24.
Marra, F., et al., "Use of tranexamic acid in total knee arthroplasty," Joints, 2016, 4(4); 202-213.
Rubio-Azpeitia, E., et al., "Adult Cells Combined With Platelet-Rich Plasma for Tendon Healing," The Orthopaedic Journal of Sports Medicine, 2017, 5(2), pp. 1-11.

* cited by examiner

*Primary Examiner* — Fereydoun G Sajjadi
*Assistant Examiner* — Joel D Levin
(74) *Attorney, Agent, or Firm* — DUANE MORRIS LLP; Gregory M. Lefkowitz; Brandon A. Chan

(57) ABSTRACT

The present disclosure relates to a pharmaceutical composition for preventing or treating musculoskeletal disease, which has the effect of proliferating endogenous cells in bone marrow. More specifically, the pharmaceutical composition of the present disclosure can be used for the treatment of musculoskeletal disease since it proliferates endogenous cells in bone marrow and enhances the functions thereof.

12 Claims, 18 Drawing Sheets

BM MSC (P0) CFU-F Assay

Affected
_before injection

Contralateral normal
_w/o PRP injection

Affected
_w/ PRP injection

CFU-F Assay at P0

Contralateral normal
_w/o PRP injection

Affected
_w/ PRP injection

CFU-F Assay at P1

Contralateral normal
_w/o PRP injection

Affected
_w/ PRP injection

FIG. 3

Boyden chamber assay

Gradient of chemoattractant

Control

Example 1   SDF-1α

G-CSF   IL-1ß

*100X magnification*

100X magnification

PHARMACEUTICAL COMPOSITION USING ENDOGENOUS CELLS FOR PREVENTING OR TREATING MUSCULOSKELETAL DISORDERS

CROSS-REFERENCE TO RELATED APPLICATIONS

This application is a § 371 national stage entry of International Application No. PCT/KR2019/013906, filed on Oct. 22, 2019, which claims priority to Korean Patent Application No. 10-2019-0003742, filed on Jan. 11, 2019, the entire contents of which are incorporated herein by reference.

TECHNICAL FIELD

The present disclosure relates to a pharmaceutical composition for preventing or treating musculoskeletal disease, which has the effect of proliferating endogenous cells in bone marrow. More specifically, the pharmaceutical composition of the present disclosure can be used for the treatment of musculoskeletal disease since it proliferates endogenous cells in bone marrow and enhances the functions thereof.

BACKGROUND ART

The musculoskeletal system collectively refers to nerve, tendon, muscle, bone, ligament, cartilage, etc. Musculoskeletal diseases occur in the nerves, muscles and nearby bodily tissues of the neck, shoulders, waist and limbs due to injury, degeneration and deformation caused by repeated movements, improper working postures, use of undue force, contact with sharp edges, vibrations, heat, overuse, trauma, aging, etc.

The tendon and ligament are fibrous soft tissues made up mostly of collagen. They are very similar not only in mechanical properties but also in structures, differing only in that the tendon connects muscle to bone whereas the ligament connects one bone to another.

The tendon and ligament require a very long time for regeneration if damaged and it is reported that they do not fully recover their functions after the regeneration, because the supply of blood is relatively insufficient as compared to other tissues, the number of cells is small as compared to the matrix, and the matrix cells are highly differentiated cells.

In the US, about 7 billion dollars are spent annually in direct cost of treatment of tendon injuries of the shoulders. In particular, rotator cuff disease is the commonest cause, with 4.5 million hospital visits, about 300,000 surgeries and 3 billion dollars of cost annually. The most typical surgery for rotator cuff disease is subacromial decompression. It is performed more frequently than meniscal knee surgery or total knee replacement (TKR), ranking second among all musculoskeletal system surgeries. It is expected to increase more in the 2010s.

The currently available methods for treating musculoskeletal diseases including rotator cuff disease are mostly symptomatic treatments that only treat the symptoms, not the underlying cause. Focus is made on alleviating inflammation through rest, anti-inflammatory drugs, steroids, etc. in the early stage, and surgical treatment is made after tear has occurred.

These therapeutic methods have at least four distinct problems. First, despite the term 'tendinitis' commonly used in tendon diseases, common inflammatory cells are hardly found. Accordingly, the medication of anti-inflammatory drugs or steroids may have almost no effect. In addition, since the symptomatic treatment treatments cannot solve the still unclear underlying cause of tendon diseases, little effect is achieved for chronic tendon diseases. Even when surgical treatment is made after tear has occurred, it is only a temporary measure rather than the cure of underlying cause. Lastly, although rotator cuff repair shows relatively good clinical results, retare occurs in about 27-94% within 1-2 years after the surgery.

Various biological treatment methods have been developed to overcome the problems and limitations described above. For example, therapies using exogenous or endogenous stem cells are being researched by many researchers. However, one of the common problems of the therapies using exogenous or endogenous stem cells is that it is difficult to supply a sufficient number of stem cells. That is to say, effective treatment cannot be achieved since the number of stem cells present in the bone marrow is very small in normal state and, even when bone marrow stimulation procedures such as multiple channeling or microfracture surgery are performed, the therapeutic effect is insignificant because the number of stem cells migrating to lesions is small. At present, it is very difficult to overcome these problems.

In addition, for the elderly in which musculoskeletal diseases occur mainly, the therapeutic effect for the musculoskeletal system cannot be exerted properly because the number of endogenous cells such as stem cells is decreased further and the proliferability of the endogenous cells is remarkably low for chronic diseases such as osteoarthritis, etc.

In order to compensate for these problems and disadvantages, the autologous matrix-induced chondrogenesis (AMIC) method of treating with hyaluronic acid or applying a collagen III/I membrane following a surgery such as microfracture surgery has been developed to maintain stem cells in the lesions and prevent the loss of stem cells to the microfractured area. However, it has been found out that no appreciable result is achieved and inflammatory responses are induced on the contrary.

Besides, although a method of treating tendon or ligament diseases by using a collagen membrane or a bilayer support containing growth factors is known, it has not been verified how much the loss of stem cells can be prevented. And, even if it is possible, the effect is not great because the number of stem cells in the bone marrow of the lesion site is very small. Therefore, the development of a new therapy is necessary.

In order to solve the problems described above and develop a new therapeutic agent for treating musculoskeletal diseases, the number of endogenous cells should be increased first of all. However, since most of the existing therapeutic methods utilizes endogenous cells or compositions for preventing the loss of endogenous cells, they are very limited in terms of therapeutic effect or target diseases because there are few endogenous cells such as stem cells in the lesions.

The information described in the background section is only for enhancing the understanding of the background of the present disclosure and it should not be construed as admitting that it is prior art known to those having ordinary knowledge in the art.

DISCLOSURE

Technical Problem

The inventors of the present disclosure have made consistent efforts to discover a new therapeutic agent for a musculoskeletal disease, which contains platelet-rich plasma (PRP) as an active ingredient. As a result, they have devised a pharmaceutical composition containing platelet-rich plasma (PRP), batroxobin, calcium and tranexamic acid, and have completed the present disclosure by identifying that endogenous cells are proliferated and the symptoms of a patient are alleviated and treated when the composition is injected to the affected part.

Accordingly, the present disclosure is directed to providing a pharmaceutical composition for preventing or treating a musculoskeletal disease, which contains platelet-rich plasma (PRP), batroxobin, calcium and tranexamic acid as active ingredients.

The present disclosure is also directed to providing a pharmaceutical composition for preventing or treating a musculoskeletal disease of a non-human animal, which contains platelet-rich plasma (PRP), batroxobin, calcium and tranexamic acid as active ingredients.

The present disclosure is also directed to providing a method for treating a musculoskeletal disease, which includes administering the composition to human or a non-human animal.

The present disclosure is also directed to providing a novel use of a composition containing platelet-rich plasma (PRP), batroxobin, calcium and tranexamic acid for preparation of a medication for human or an animal for treating a musculoskeletal disease.

The present disclosure is also directed to providing a pretreatment composition and an adjuvant for treating a musculoskeletal disease, which contain platelet-rich plasma (PRP), batroxobin, calcium and tranexamic acid as active ingredients and are used to enhance the growth of endogenous cells in the musculoskeletal system.

The present disclosure is also directed to providing a method for preparing the pharmaceutical composition for preventing or treating a musculoskeletal disease.

Other purposes and advantages of the present disclosure will become more apparent by the following detailed description, claims and drawings.

Technical Solution

The present disclosure provides a pharmaceutical composition for preventing or treating a musculoskeletal disease, which contains platelet-rich plasma (PRP), batroxobin, calcium and tranexamic acid as active ingredients.

In an exemplary embodiment of the present disclosure, a mixing weight ratio of the platelet-rich plasma (PRP), the batroxobin, the calcium and the tranexamic acid may be 10-20:1-4:1:1-3.

In an exemplary embodiment of the present disclosure, the platelet-rich plasma (PRP) may be autologous or allogeneic.

In an exemplary embodiment of the present disclosure, the concentration of the platelet-rich plasma (PRP) may be $200\text{-}5,000\times10^3$ platelets/microL.

In an exemplary embodiment of the present disclosure, the pharmaceutical composition may be a gel-type injection injected to an affected part.

In an exemplary embodiment of the present disclosure, the affected part may be a bone-tendon junction or a bone-ligament junction.

In an exemplary embodiment of the present disclosure, the affected part may be an intraosseous passage formed through multiple channeling.

In an exemplary embodiment of the present disclosure, the musculoskeletal disease may be one or more selected from a group consisting of a muscular disease, a tendon disease, a cartilage disease, a joint disease, a ligament disease and a disease induced by the injury and deformation of nerve, muscle, tendon, ligament, bone, cartilage, meniscus or joint.

In an exemplary embodiment of the present disclosure, the musculoskeletal disease may be one or more selected from a group consisting of Achilles tendon disease, patellar tendon disease, lateral epicondylitis, medial epicondylitis, plantar fasciitis, rotator cuff tendon disease, tenosynovitis, tendinosis, tendinitis, peritenonitis, tendon injury, tendon sprain, tendon rupture, tendon tear, tendon exfoliation, cruciate ligament injury, ankle ligament injury, collateral ligament injury, ligament rupture, ligament sprain, chondromalacia, osteoarthritis, arthrosis deformans, dyschondroplasia, degenerative arthritis, rheumatoid arthritis, osteomalacia, fibrous ostitis and aplastic bone disease.

In an exemplary embodiment of the present disclosure, the pharmaceutical composition may facilitate the proliferation of endogenous cells.

The present disclosure also provides a pharmaceutical composition for preventing or treating a musculoskeletal disease of a non-human animal, which contains platelet-rich plasma (PRP), batroxobin, calcium and tranexamic acid as active ingredients.

The present disclosure also provides a method for treating a musculoskeletal disease by administering a composition containing platelet-rich plasma (PRP), batroxobin, calcium and tranexamic acid to human or a non-human animal.

The present disclosure also provides a novel use of a composition containing platelet-rich plasma (PRP), batroxobin, calcium and tranexamic acid for preparation of a medication for human or an animal for treating a musculoskeletal disease.

The present disclosure also provides a pretreatment composition for repairing the musculoskeletal system, which contains platelet-rich plasma (PRP), batroxobin, calcium and tranexamic acid as active ingredients and is used to proliferate endogenous cells in the bone marrow of the musculoskeletal system.

The present disclosure also provides an adjuvant for repairing the musculoskeletal system, which contains platelet-rich plasma (PRP), batroxobin, calcium and tranexamic acid as active ingredients and is used to proliferate endogenous cells in the bone marrow of the musculoskeletal system.

The present disclosure also provides a method for preparing a pharmaceutical composition for preventing or treating a musculoskeletal disease, which includes a step of mixing platelet-rich plasma (PRP), batroxobin, calcium and tranexamic acid.

In an exemplary embodiment of the present disclosure, the platelet-rich plasma (PRP), the batroxobin, the calcium and the tranexamic acid may be mixed at a weight ratio of 10-20:1-4:1:1-3.

Advantageous Effects

The features and advantages of the present disclosure may be summarized as follows:

(i) The present disclosure provides a pharmaceutical composition for preventing or treating a musculoskeletal system disease, which contains platelet-rich plasma (PRP), batroxobin, calcium and tranexamic acid as active ingredients.

(ii) The present disclosure also provides a pretreatment composition for treating a musculoskeletal disease, specifically a pretreatment composition for repairing the musculoskeletal system, which contains platelet-rich plasma (PRP), batroxobin, calcium and tranexamic acid as active ingredients and is used to facilitate the proliferation of endogenous cells in the musculoskeletal system.

(iii) The composition of the present disclosure is a safe substance capable of exhibiting effective therapeutic effect on musculoskeletal diseases caused by various reasons despite the small number of endogenous cells and exhibits therapeutic effect in an in-vivo experiment on patients with ruptured rotator cuff tendon. Therefore, it can be usefully used as a therapeutic agent for the diseases of the musculoskeletal system such as injury, rupture, etc.

BRIEF DESCRIPTION OF DRAWINGS

FIG. 3 shows the result of colony-forming unit-fibroblast (CFU-F) assay for cells isolated from bone marrow taken from a patient after subculturing (P1) before and after the administration of a composition prepared in Example 1

BEST MODE

Figure 1:
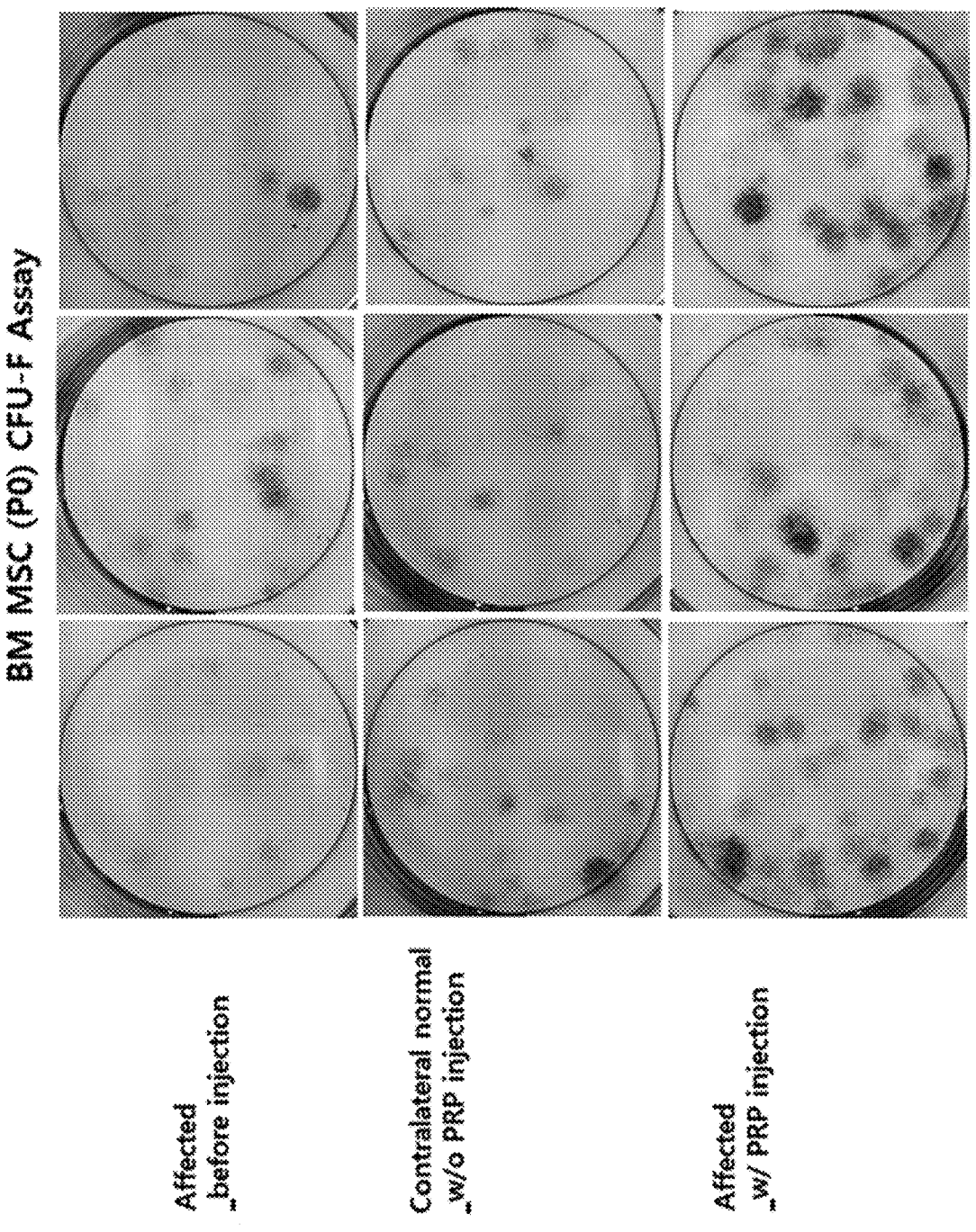
FIG. 1 shows the result of colony-forming unit-fibroblast (CFU-F) assay for bone marrow taken from a patient before and after the administration of a composition prepared in Example 1.

In an aspect, the present disclosure provides a pharmaceutical composition for preventing or treating a musculoskeletal disease, which contains platelet-rich plasma (PRP), batroxobin, calcium and tranexamic acid as active ingredients.

The inventors of the present disclosure have made efforts to discover a substance which exhibits effective therapeutic effect on musculoskeletal diseases caused by various reasons despite the small number of endogenous cells and can be prescribed safely. As a result, they have identified that a composition containing platelet-rich plasma (PRP), batroxobin, calcium and tranexamic acid as active ingredients exhibits very superior effect of treating musculoskeletal diseases by restoring the proliferation and function of endogenous cells without loss of cells at the lesion site.

In the present disclosure, the term "endogenous cells" collectively refers to cells existing in the bone marrow of the lesion site. It includes stem cells, differentiated cells, cells intermediate between stem cells and differentiated cells. Specifically, it may refer to stem cells mainly existing in the bone marrow.

In the present disclosure, the term activity of preventing or treating a "musculoskeletal disease" refers to an activity of preventing, alleviating or treating a musculoskeletal disease induced by the injury or damage of the musculoskeletal system. Specifically, it means inducing a favorable clinical or therapeutic effect of alleviating a pathological condition to be treated, delaying the progression thereof, accelerating the healing thereof, improving the healing response thereof, recovering the pathological condition, ameliorating the pain associated with the injured musculoskeletal system, increasing the range of motion of the affected joint, or proliferating and recovering the function of endogenous cells, particularly stem cells, present in the affected part.

The musculoskeletal disease includes a damage to the nerve, muscle, tendon, ligament, bone, cartilage, meniscus, joint and nearby tissues and a degenerative or intractable disease induced thereby, although not being specially limited thereto.

The musculoskeletal disease occurs also in young and middle-aged adults due to repeated movements and continued improper postures. However, it occurs mainly as a degenerative disease in the elderly. The disease is often accompanied by pain during work or rest.

The muscular disease may be an amyotrophic disease. For example, it includes one or more selected from a group consisting of muscular atrophy, myopathy, muscular injury, muscular dystrophy, myasthenia, sarcopenia, myoneural conductive disease, dermatomyositis, diabetic amyotrophy, nerve injury, amyotrophic lateral sclerosis (ALS), cachexia and degenerative muscle disease, although not being limited thereto.

The tendon disease collectively refers to a disease caused by the injury of a tendon, which is a connective tissue that connects muscle to bone, excessive exercise or bacterial infection.

The tendon may be one or more selected from a group consisting of patellar tendon, tibialis anterior tendon, Achilles tendon, hamstring tendon, semitendinosus tendon, gracilis tendon, supinator tendon, adductor tendon, supraspinatus tendon, infrasupinatus tendon, subscapularis tendon, teres minor tendon (rotator cuff complex), various flexor tendons and extensor tendons of limbs and limb joints including extensor carpi radialis longus tendon, extensor carpi radialis brevis tendon, flexor carpi radialis tendon and flexor carpi ulnaris tendon, quadriceps tendon and posterior tibial tendon. In some exemplary embodiments, the tendon may be one or more selected from a group consisting of patellar tendon, tibialis anterior tendon, Achilles tendon, hamstring tendon, semitendinosus tendon, gracilis tendon, supinator tendon and adductor tendon. And, in another exemplary embodiment, the tendon may be one or more selected from a group consisting of supraspinatus tendon, infrasupinatus tendon, subscapularis tendon, teres minor tendon (rotator cuff complex), flexor tendon, rectus femoris tendon, posterior tibial tendon and quadriceps tendon.

Specifically, the tendon disease may include one or more selected from a group consisting of Achilles tendon disease, patellar tendon disease, lateral epicondylitis, medial epicondylitis, plantar fasciitis, rotator cuff tendon disease, tenosynovitis, tendinosis, tendinitis, peritenonitis, tendon injury, tendon sprain, tendon rupture, tendon tear and tendon exfoliation, although not being limited thereto.

The ligament to which the pharmaceutical composition of the present disclosure may be applied is not particularly limited. For example, it may be one or more selected from a group consisting of coracoclavicular ligament, glenohumeral ligament, anterior cruciate ligament, lateral collateral ligament, posterior cruciate ligament, medial collateral ligament, caudal cruciate ligament, cricothyroid ligament, periodontal ligament, suspensory ligament of the lens, anterior sacroiliac ligament, posterior sacroiliac ligament, sacrotuberous ligament, sacrospinous ligament, inferior pubic ligament, medial and lateral collateral ligaments of limb joints, superior pubic ligament, suspensory ligaments (e.g., penis or breast), palmar radiocarpal ligament, dorsal radiocarpal ligament, ulnar collateral ligament, radial collateral ligament, triangular ligament and ligaments of the ankle such as anterior talofibular ligament.

The cartilage disease may be a cartilage disease caused by the injury of cartilage tissue. Specifically, it may be selected from a group consisting of chondromalacia, osteoarthritis, arthrosis deformans, dyschondroplasia, degenerative arthritis, rheumatoid arthritis, osteomalacia, fibrous ostitis and aplastic bone disease, although not being limited thereto.

The joint disease may be one or more selected from a group consisting of degenerative arthritis, rheumatoid arthritis, fracture, damage of muscular tissue, plantar fasciitis, tennis elbow, myositis ossificans, nonunion of fracture and joint injury caused by trauma.

In addition, the musculoskeletal disease may further include diseases caused by the injury and deformation of nerve, muscle, tendon, ligament, bone, cartilage, meniscus and joint.

According to an example of the present disclosure, the composition of the present disclosure exhibited a therapeutic effect for rotator cuff tendon in an in-vivo experiment on a patient having ruptured rotator cuff tendon. The composition exhibited therapeutic effect in terms of (1) decreased pain, (2) increased range of joint motion, (3) muscular power and (4) function of frequently used six shoulder joint one year after the administration (Experimental Example 7).

In the present disclosure, a mixing weight ratio of the platelet-rich plasma (PRP), the batroxobin, the calcium and the tranexamic acid may be specifically 10-20:1-4:1:1-3. If any of the four ingredients of the present disclosure is not included, long time may be required for gelation or contraction. When a composition having such a problem is injected into the body, the recruitment (or homing) and proliferation of endogenous stem cells cannot be induced and, on the contrary, the loss of endogenous cells, particularly stem cells, may be facilitated. Therefore, it is the most preferred that the composition contains platelet-rich plasma, calcium, batroxobin and tranexamic acid.

Specifically, as a result of investigating various therapeutic effects of the composition containing platelet-rich plasma, calcium, batroxobin and tranexamic acid as active ingredients according to the present disclosure such as secretion of platelet-derived growth factor and proliferation and functional recovery of endogenous cells in addition to gelation and contraction, platelet-derived growth factor was secreted for a long period of time (1-14 days) at a relatively higher concentration. When batroxobin and tranexamic acid were not mixed, a significantly smaller amount of platelet-derived growth factor was secreted. The secretion amount was decreased rapidly from day 7 and an undetectable amount or a trace amount was detected from day 10. Therefore, it is difficult to achieve a sufficient therapeutic effect when any of the four ingredients of the present disclosure is not contained since the secretion period of platelet-derived growth factor is shortened significantly.

For example, when batroxobin and tranexamic acid were not included, platelet-derived growth factor was secreted at a low concentration for only a short period of time eve when other ingredients were mixed at the same ratio as the composition of the present disclosure (Experimental Example 3).

When a composition was prepared by mixing platelet-rich plasma with hyaluronic acid or thrombin as the existing gel preparation, the ability of proliferating endogenous cells was remarkably lower than the composition of the present disclosure even when calcium was present. In addition, a long time of 14 days or longer was required to ensure sufficient ability of proliferating endogenous cells (Experimental Example 4).

In addition, it is the most preferred that the composition of the present disclosure contains calcium and batroxobin or tranexamic acid at a mixing volume ratio of 1:2. This can be confirmed from the result that, among the compositions containing calcium and batroxobin at ratios of 1:2, 2:2 and 1:4, the one with a mixing ratio of 1:2 exhibits the best effect of proliferating endogenous cells including stem cells, etc. (Experimental Example 4).

The platelet-rich plasma (PRP), which is an active ingredient of the pharmaceutical composition of the present disclosure, is not particularly limited as long as it is one prepared by a common method. In the present disclosure, a standard and consistent plateletpheresis system with a leukoreduction set (COBE Spectra LRS Turbo, Caridian BCT, Lakewood, Colorado) was used to isolate the platelet-rich plasma.

Specifically, the platelet-rich plasma (PRP) may be autologous or allogeneic. More specifically, the platelet-rich plasma may be a plasma rich in platelets, obtained by separating whole blood by centrifugation and taking the lower layer abundant in platelets. The platelet-rich plasma may be obtained by taking autologous or allogeneic whole blood, centrifuging the same with an ultracentrifuge and recovering the supernatant. The platelet-rich plasma may be centrifuged further depending on the desired concentration. Since it is preferred that the platelet-rich plasma (PRP) has a concentration of 200-5,000×10$^3$ platelets/microL, concentrated platelet-rich plasma may be diluted to achieve the desired concentration.

The platelet-rich plasma is one obtained by physically concentrating platelets, wherein the platelet-derived growth factors enhancing the proliferation and functional recovery of endogenous cells are not substantially activated. For activation and secretion of the large quantity of platelet-derived growth factors present in platelets, the platelets should be activated first. In general, activating factors such as calcium chloride, thrombin, collagen, serotonin, adenosine diphosphate (ADP), acetylcholine (ACH), etc. have been used to activate the platelets in platelet-rich plasma. However, as described above, the composition of the present disclosure should necessarily contain batroxobin and tranexamic acid. If any of the ingredients is missing, gelation or contraction may not occur or a long time may be required for the gelation or contraction. When a composition having such a problem is injected into the body, the recruitment (or homing) and proliferation of endogenous stem cells cannot be induced and, on the contrary, the loss of endogenous cells, particularly stem cells, may be facilitated.

The composition of the present disclosure may be prepared into a gel-type injection injected to the affected part. Specifically, the composition of the present disclosure may be applied to the desired part via a syringe, a needle or a cannula. When applying the composition of the present disclosure to the affected part, the affected part may be bone-tendon junction or bone-ligament junction. That is to say, the site at which the composition of the present disclosure is administered should be prepared surgically by perforating or piercing the affected part. Specifically, an intraosseous hole or passage may be formed at the affected part through multiple channeling.

In the present disclosure, the term "pharmaceutically effective amount" or "therapeutically effective amount" means an amount sufficient to achieve the effect or activity of the composition containing platelet-rich plasma (PRP), batroxobin, calcium and tranexamic acid. Since the composition according to the present disclosure has no side effect to the human body even when administered in excess amount, the upper limit of the amount of the platelet-rich plasma (PRP), batroxobin, calcium and tranexamic acid contained in the composition of the present disclosure may be adequately determined by those skilled in the art.

An appropriate administration dosage of the pharmaceutical composition of the present disclosure varies depending on the age, body weight, sex, pathological condition and diet of a patient, administration time, administration route, and response sensitivity such as excretion rate. An ordinarily skilled physician can easily determine and prescribe an administration dosage effective for the desired treatment or prevention. According to a specific exemplary embodiment of the present disclosure, a single administration dosage of the pharmaceutical composition of the present disclosure is 0.001-100 mg/kg.

In addition, the present disclosure provides a pharmaceutical composition for preventing or treating a musculoskeletal disease of a non-human animal, which contains platelet-rich plasma (PRP), batroxobin, calcium and tranexamic acid as active ingredients.

In addition, the present disclosure provides a novel use of a composition containing platelet-rich plasma (PRP), batroxobin, calcium and tranexamic acid for preparation of a medication for human or an animal for preventing or treating a musculoskeletal disease.

In addition, the present disclosure provides a method for treating a musculoskeletal disease, which includes a step of administering a therapeutically effective amount of a composition containing platelet-rich plasma (PRP), batroxobin, calcium and tranexamic acid to human or a non-human animal.

The composition according to the present disclosure can be prescribed safely because it exhibits effective therapeutic effect on the injury or disease of the musculoskeletal system despite the few number of endogenous cells and can be usefully used to treat and prevent a musculoskeletal disease by recovering the proliferation and function of endogenous cells without loss of the cells existing at the lesion site.

The musculoskeletal disease includes a damage to the nerve, muscle, tendon, ligament, bone, cartilage, meniscus, joint and nearby tissues and a degenerative or intractable disease induced thereby, although not being specially limited thereto. More details can be referred to the foregoing description on the pharmaceutical composition.

As a result of investigating various therapeutic effects of the 'medication', 'pharmaceutical composition for an animal' or 'medication for an animal' including not only gelation and contraction but also the secretion period of platelet-derived growth factor, proliferation and functional recovery of endogenous cells, etc., it was found out that, when any of the four ingredients of the present disclosure is missing, it is difficult to achieve sufficient therapeutic effect because the secretion period of platelet-derived growth factor is decreased significantly.

The composition of the present disclosure may be prepared as a gel-type injection injected to the affected part. Specifically, the composition of the present disclosure may be applied to the desired part via a syringe, a needle or a cannula. When applying the composition of the present disclosure to the affected part, the affected part may be bone-tendon junction or bone-ligament junction. That is to say, the site at which the composition of the present disclosure is administered should be prepared surgically by perforating or piercing the affected part. Specifically, an intraosseous hole or passage may be formed at the affected part through multiple channeling.

The administration dosage of the medication, pharmaceutical composition for an animal or medication for an animal may vary depending on the age, sex and body weight of a patient or an animal to be treated. Above all, it will vary depending on the condition of the subject to be treated, the particular category or type of the disease to be treated, administration route, or the characteristics of the used therapeutic agent.

The administration dosage of the medication, pharmaceutical composition for an animal or medication for an animal may be determined adequately depending on the absorption rate and excretion rate of the active ingredients in the body, the age, body weight, sex and condition of a patient or an animal to be treated, the severity of a disease to be treated, etc. Specifically, a single administration dosage may be 0.001-100 mg/kg in general. If necessary, the administration may be made several times with predetermined intervals.

The medication, pharmaceutical composition for an animal or medication for an animal may be administered as a prophylactic agent or a therapeutic agent either alone or in combination with another therapeutic agent. The co-administration with another therapeutic agent may be made sequentially or simultaneously.

In the method for treating a musculoskeletal disease, the composition may be administered parenterally to human or a non-human animal, particularly a mammal. For example, the composition may be administered parenterally to the desired part using a syringe, a needle or a cannula. When applying the composition of the present disclosure to the affected part, the affected part may be bone-tendon junction or bone-ligament junction. That is to say, the site at which the composition of the present disclosure is administered should be prepared surgically by perforating or piercing the affected part. Specifically, an intraosseous hole or passage may be formed at the affected part through multiple channeling.

For the administration dosage, administration method and number of administration for the treatment, the foregoing description on the administration dosage, administration method and number of administration for the pharmaceutical composition, medication, pharmaceutical composition for an animal or medication for an animal may be referred to.

The present disclosure may also provide a pretreatment composition and an adjuvant for treating a musculoskeletal disease, which contain platelet-rich plasma (PRP), batroxobin, calcium and tranexamic acid as active ingredients and are used to proliferate endogenous cells in the musculoskeletal system. The 'treatment of a musculoskeletal disease' includes drug administration, operation or surgery for treating a musculoskeletal disease. Specifically, the treatment of a musculoskeletal disease may be operation or surgery for repairing the musculoskeletal system, although not being specially limited thereto. Most specifically, it may be musculoskeletal system repair.

Various surgical methods have been developed for treatment of musculoskeletal diseases. However, if a patient is in acute phase or old-aged, or if the amount of endogenous cells present in the bone marrow at the affected part is too small, surgical operation may be limited or the therapeutic effect of the surgical operation may be insignificant because the expression and secretion of platelet-derived growth factor that can prevent or treat the damage and disease of the musculoskeletal system are insufficient. Although a therapeutic method of administering endogenous cells or platelet-rich plasma has been developed to overcome this disadvantage, treatment of a musculoskeletal disease has been substantially unsuccessful because the endogenous cells or platelet-rich plasma are not retained at the affected part but are absorbed into the body or flow to other parts and, therefore, platelet-derived growth factors cannot be supplied for a period of time enough for treatment.

In order to solve this problem, a technology of adding a vehicle such as hyaluronic acid, thrombin, etc. to the endogenous cells, platelet-rich plasma, etc., has been developed. However, no appreciable result has been achieved and poor prognosis such as inflammatory responses, etc. has been observed.

With the aging of the modern society, the cases where operation or surgery is difficult or prognosis is poor after operation or surgery are increasing due to the low content of endogenous stem cells. Therefore, the development of a new therapeutic agent or therapeutic method that can enhance the therapeutic effect of surgical operation for a musculoskeletal disease regardless of the content of endogenous cells existing at the affected part by supplying platelet-derived growth factors of a sufficiently high concentration during long-term treatment and, thereby facilitating the proliferation and functional recovery of endogenous cells at the affected part, is necessary.

The present disclosure also relates to a pretreatment or adjuvant composition for operation or surgery for musculoskeletal system repair, which can maximize the therapeutic effect or treatment period even when the content of endogenous cells existing at the affected part is low, increase the success rate of operation or surgery, and reduce the risk of recurrence after the treatment. Most specifically, it may relate to a pretreatment or adjuvant composition for tendon or ligament repair.

It was confirmed through various experiments that the pretreatment composition for repairing the musculoskeletal system for treatment of a musculoskeletal disease, the pretreatment composition for repairing the musculoskeletal system for treatment of a musculoskeletal damage or an adjuvant thereof, which contains platelet-rich plasma (PRP), batroxobin, calcium and tranexamic acid, can provide safe, convenient and effective treatment by quickly maximizing and consistently maintaining the proliferation and functional recovery of endogenous cells at the affected part (tendon, ligament, or junctions thereof to bone) where the concentration of the endogenous cells is significantly low and that a tendon or ligament disease can be treated effectively by improving the concentration of endogenous cells by administering the composition before conducting surgical operation.

The surgery or repair of the musculoskeletal system includes common surgeries for treating and recovering the damage to muscle, tendon, ligament, cartilage, joint or nearby tissues or a degenerative or intractable disease induced by the damage or deformation. For example, it may be one or more selected from a group consisting of tendon or ligament repair, arthroscopic repair, minimum incision repair, local tendon transposition, local tendon replacement, tendon transfer, latissimus dorsi transfer, capsular shift, replacement arthroplasty, hemiarthroplasty, reverse shoulder arthroplasty, ligament reconstruction, acromioplasty, hemi-arthroplasty of the hip and surgery of femoral fracture.

Specifically, the present disclosure may provide a therapeutic method including a step of administering the composition of the present disclosure to a patient before or after surgery or repair for treating a musculoskeletal disease. More specifically, the composition may be administered before or during the surgery or repair for treating a musculoskeletal disease. The surgery, repair or operation for treating a musculoskeletal disease may be operation for attachment or reattachment to nerve, muscle, tendon, ligament, cartilage, meniscus, joint or nearby tissues. Specifically, it may be rotator cuff repair, open rotator cuff repair, minimally open rotator cuff repair, arthroscopic repair, etc., although not being specially limited thereto.

Specifically, the composition of the present disclosure may be injected to the affected part. The affected part may be at least one small hole or passage formed near the junction with tendon or ligament through multiple channeling (or microfracture surgery). The composition of the present disclosure may be administered through the hole or passage.

According to another aspect, the present disclosure provides a method for preparing a pharmaceutical composition for preventing or treating a musculoskeletal disease, which includes a step of mixing platelet-rich plasma (PRP), batroxobin, calcium and tranexamic acid, wherein the platelet-rich plasma (PRP), the batroxobin, the calcium and the tranexamic acid are mixed at a weight ratio of 10-20:1-4:1:1-3.

According to another aspect, the present disclosure provides a kit for treating a musculoskeletal disease, which includes a composition containing platelet-rich plasma (PRP), batroxobin, calcium and tranexamic acid.

The composition containing platelet-rich plasma (PRP), batroxobin, calcium and tranexamic acid contains platelet-rich plasma of a specific concentration. The concentration of the platelet-rich plasma may be predetermined depending on the characteristics of the musculoskeletal injury and disease to be treated.

The kit may further include a syringe. The syringe may allow easy injection or administration of a composition containing platelet-rich plasma (PRP), batroxobin, calcium and tranexamic acid for application to a surgical site, e.g., musculoskeletal system (muscle, tendon, ligament, cartilage, joint or nearby tissues). The kit may further include an instruction.

Mode for Invention

Hereinafter, the present disclosure will be described in detail through examples. It will be apparent to those having ordinary skill in the art that those examples are only for describing present disclosure in more detail and the scope of the present disclosure is not limited by the examples.

EXAMPLES

<Preparation Example 1> Preparation of Platelet-Rich Plasma (PRP)

Platelet-rich plasma (PRP) was isolated using a plateletpheresis system with a leukoreduction set (COBE Spectra LRS Turbo, Caridian BCT, Lakewood, Colorado). The concentration of platelets was $1,400 \times 10^3$ per microliter and ACD-A solution was used as an anticoagulant. For clinical experiment, the isolated platelet-rich plasma was concentrated to a concentration of $5,000 \times 10^3$ platelets/microL and then stored. Then, it was diluted to a desired concentration for experiment.

Prior to experiment, the platelet-rich plasma was subjected to hepatitis B, hepatitis C, human immunodeficiency virus and syphilis tests for safety evaluation.

<Examples and Comparative Examples> Preparation of Composition Containing Platelet-Rich Plasma, Calcium, Batroxobin and Tranexamic Acid The gelation characteristics of a composition containing platelet-rich plasma, calcium, batroxobin and tranexamic acid depending on mixing ratio was investigated.

The platelet-rich plasma prepared and stored in Preparation Example 1 was used after diluting to a concentration of $1,000\text{-}1,400 \times 10^3$ platelets/microL. As calcium (Ca), calcium gluconate purchased from JW Pharmaceutical was used. As batroxobin (BTX), Botropase purchased from Hanlim Pharm was used. Tranexamic acid (TXA) was purchased from Daihan Pharm. As thrombin (THRB), freeze-dried thrombin powder was purchased from Reyon Pharmaceutical and used after diluting to a concentration of 166.67 IU. Compositions of Examples and Comparative Examples were prepared by mixing platelet-rich plasma, calcium, batroxobin and tranexamic acid at various volume ratios as described in Table 1. Hyaluronic acid was purchased from LG Life Sciences.

TABLE 1

|  | Platelet-rich plasma (mL) | Batroxobin (mL) | Calcium (mL) | Tranexamic acid (mL) | Thrombin (mL) | Hyaluronic acid (mL) |
|---|---|---|---|---|---|---|
| Example 1 | 2 | 0.2 | 0.1 | 0.23 | — | — |
| Example 2 | 2 | 0.2 | 0.2 | 0.24 | — | — |
| Example 3 | 2 | 0.4 | 0.1 | 0.25 | — | — |
| Example 4 | 2 | 0.4 | 0.2 | 0.26 | — | — |
| Example 5 | 2 | 1 | 0.1 | 0.31 | — | — |
| Example 6 | 2 | 1 | 0.2 | 0.32 | — | — |
| Comparative Example 1 | 2 | 0.2 | 0 | 0 | — | — |
| Comparative Example 2 | 2 | 0.2 | 0 | 0.22 | — | — |
| Comparative Example 3 | 2 | 0.2 | 0.1 | 0 | — | — |
| Comparative Example 4 | 2 | 0.2 | 0.2 | 0 | — | — |

TABLE 1-continued

|  | Platelet-rich plasma (mL) | Batroxobin (mL) | Calcium (mL) | Tranexamic acid (mL) | Thrombin (mL) | Hyaluronic acid (mL) |
|---|---|---|---|---|---|---|
| Comparative Example 5 | 2 | 0.4 | 0 | 0 | — | — |
| Comparative Example 6 | 2 | 0.4 | 0.1 | 0 | — | — |
| Comparative Example 7 | 2 | 0.4 | 0.2 | 0 | — | — |
| Comparative Example 8 | 2 | 0.4 | 0 | 0.24 | — | — |
| Comparative Example 9 | 2 | 1 | 0 | 0 | — | — |
| Comparative Example 10 | 2 | 1 | 0 | 0.3 | — | — |
| Comparative Example 11 | 2 | 1 | 0.1 | 0 | — | — |
| Comparative Example 12 | 2 | 1 | 0.2 | 0 | — | — |
| Comparative Example 13 | 2 | 0 | 0.2 | 0 | — | — |
| Comparative Example 14 | 2 | 0 | 0.2 | 0.22 | — | — |
| Comparative Example 15 | 2 | 0 | 0.2 | 0 | 166.67 IU | — |
| Comparative Example 16 | 2 (platelet-poor plasma) | 0.2 | 0.2 | 0 | — | — |
| Comparative Example 17 | 2 | 0 | 0 | 0 | — | 2 |
| Comparative Example 18 | 2 | 0 | 0.2 | 0 | — | 2 |

<Experimental Example 1> Characterization of Platelet-Rich Plasma (PRP) Prepared in Preparation Example 1

After separating the platelet-rich plasma (PRP) prepared in Preparation Example 1 into whole blood and platelet-poor plasma (PPP), the mean concentrations of platelets, red blood cells and white blood cells were measured by complete blood count using an automated hematology analyzer (XE-2100, Sysmex Corp, Kobe, Japan). The result is shown in Table 2. The data were represented by mean±standard deviation.

TABLE 2

|  | Platelet concentration ($\times 10^3$/μL) | Red blood cell concentration ($\times 10^6$/μL) | White blood cell concentration ($\times 10^6$/μL) | Fibrinogen concentration (mg/dL) |
|---|---|---|---|---|
| Whole blood | 207.33 ± 14.22 | 4.80 ± 0.39 | 7.64 ± 2.06 | 244.95 ± 61.57 |
| Platelet-rich plasma | 1,050.00 ± 234.80 | 0.18 ± 0.07 | 0.03 ± 0.03 | 258.18 ± 58.86 |
| Platelet-poor plasma | 4.75 ± 2.22 | 0.00 ± 0.00 | 0.01 ± 0.00 | 236.10 ± 82.22 |

As shown in Table 2, the mean concentrations of platelets, red blood cells and white blood cells of the platelet-rich plasma were $1,050.00 \pm 234.80 \times 10^3/\mu L$, $0.18 \pm 0.07 \times 10^6/\mu L$ and $0.03 \times 0.03 \times 10^6/\mu L$, respectively.

<Experimental Example 2> Analysis of Gelation Characteristics of Composition Containing Platelet-Rich Plasma, Calcium, Batroxobin and Tranexamic Acid The gelation characteristics of the compositions containing platelet-rich plasma, calcium, batroxobin and tranexamic acid prepared in Examples 1-6 and Comparative Examples 1-16 were analyzed. The gelation time and contraction time of the compositions are described in Table 3. The gelation time was determined by measuring the time until gel was formed after the composition was prepared, and the contraction time was determined by measuring the time until the gel was contracted after the composition was prepared.

TABLE 3

|  | Platelet-rich plasma (mL) | Batroxobin (mL) | Calcium (mL) | Tranexamic acid (mL) | Thrombin (mL) | Gelation time (min) | Contraction time (min) |
|---|---|---|---|---|---|---|---|
| Example 1 | 2 | 0.2 | 0.1 | 0.23 | — | 4.5 ± 1.0 | 23.8 ± 4.8 |
| Example 2 | 2 | 0.2 | 0.2 | 0.24 | — | 7.3 ± 1.5 | 17.0 ± 1.2 |
| Example 3 | 2 | 0.4 | 0.1 | 0.25 | — | 5.3 ± 1.0 | 23.8 ± 4.8 |
| Example 4 | 2 | 0.4 | 0.2 | 0.26 | — | 3.8 ± 0.5 | 18.0 ± 1.6 |
| Example 5 | 2 | 1 | 0.1 | 0.31 | — | 3.3 ± 1.0 | 24.5 ± 3.3 |
| Example 6 | 2 | 1 | 0.2 | 0.32 | — | 3.3 ± 1.0 | 17.8 ± 2.1 |
| Comparative Example 1 | 2 | 0.2 | 0 | 0 | — | 4.7 ± 1.2 | 108.0 ± 41.6 |
| Comparative Example 2 | 2 | 0.2 | 0 | 0.22 | — | 5.3 ± 2.3 | 108.0 ± 41.6 |
| Comparative Example 3 | 2 | 0.2 | 0.1 | 0 | — | 4.5 ± 1.0 | 20.3 ± 7.1 |
| Comparative Example 4 | 2 | 0.2 | 0.2 | 0 | — | 7.8 ± 2.4 | 14.8 ± 1.5 |
| Comparative Example 5 | 2 | 0.4 | 0 | 0 | — | 3.8 ± 1.3 | na |
| Comparative Example 6 | 2 | 0.4 | 0.1 | 0 | — | 5.3 ± 1.0 | 18.8 ± 7.8 |
| Comparative Example 7 | 2 | 0.4 | 0.2 | 0 | — | 5.3 ± 1.0 | 15.5 ± 2.5 |
| Comparative Example 8 | 2 | 0.4 | 0 | 0.24 | — | 3.8 ± 1.3 | na |
| Comparative Example 9 | 2 | 1 | 0 | 0 | — | 2.3 ± 0.5 | na |
| Comparative Example 10 | 2 | 1 | 0 | 0.3 | — | 3.8 ± 2.9 | na |
| Comparative Example 11 | 2 | 1 | 0.1 | 0 | — | 4.8 ± 2.2 | 22.0 ± 3.6 |
| Comparative Example 12 | 2 | 1 | 0.2 | 0 | — | 2.8 ± 1.0 | 15.5 ± 2.5 |
| Comparative Example 13 | 2 | 0 | 0.2 | 0 | — | 20.0 ± 12.0 | 35.0 ± 7.1 |
| Comparative Example 14 | 2 | 0 | 0.2 | 0.22 | — | 16.5 ± 10.2 | 31.5 ± 5.0 |
| Comparative Example 15 | 2 | 0 | 0.2 | 0 | 166.67 IU | 2.3 ± 1.3 | 15.5 ± 6.6 |
| Comparative Example 16 | 2 (platelet-poor plasma) | 0.2 | 0.2 | 0 | — | 24.5 ± 13.7 | na |

*) na means that contraction did not occur during the measurement period.

The gelation time and contraction time of the compositions prepared in Examples 1-6 and Comparative Examples 1-16 are compared in Table 3.

Although gels were formed from the compositions prepared by mixing platelet-rich plasma (PRP) only with batroxobin (Comparatives Example 1, 5 and 9), contraction speed was significantly slower by 6 times or more as compared to the compositions of Examples 1-5 or contraction did not occur.

When only calcium was mixed in platelet-rich plasma (PRP) (Comparative Example 13), the time required for gelation and contraction was delayed by 1.25-5 times or more.

For the compositions of Comparative Examples 1, 2, 5, 8, 9 and 10 wherein calcium was not mixed, contraction did not occur properly or it took 100 minutes or longer for contraction. In addition, for the compositions of Comparative Examples 13 and 14, wherein batroxobin was not mixed, gelation speed was significantly decreased and contraction speed was also decreased.

For the compositions of Comparative Examples 3, 4, 6, 7, 11 and 12, wherein only batroxobin and calcium were mixed with platelet-rich plasma (PRP), gelation and contraction were comparable to the compositions of Examples 1-5. However, in the subsequent experiments, it was found out that the secretion or expression of platelet-derived growth factor was lower or that the effect of proliferating and functionally recovering stem cells (endogenous cells) was significantly lower.

To summarize, if any ingredient of the platelet-rich plasma, calcium, batroxobin and tranexamic acid of the present disclosure is missing, gelation and contraction may not occur or it may take very long time for gelation or contraction. When a composition having such a problem is injected into the body, the recruitment (or homing) and proliferation of endogenous stem cells cannot be induced and, on the contrary, the loss of endogenous cells, particularly stem cells, may be facilitated. Accordingly, it is the most preferred that the composition contains platelet-rich plasma, calcium, batroxobin and tranexamic acid within the ranges described above.

<Experimental Example 3> Secretion of Platelet-Derived Growth Factor with Time

The concentration (ng/mL) of platelet-derived growth factor was measured by enzyme-linked immunosorbent assay (human PDGF-AB ELISA, ELH-PDGF-2; RayBiotech, Norcross, Georgia, USA) in consideration of washing out by body fluid. The result is shown in Table 4. As a negative control group, 2 mL of the platelet-rich plasma prepared in Preparation Example 1 was used.

TABLE 4

| Concentration (ng/mL) | Ex. 1 (PRP + Ca + BTX + TXA) | Comp. Ex. 3 (PRP + Ca + BTX) | Comp. Ex. 14 (PRP + Ca + THRB) | Comp. Ex. 13 (PRP + Ca) | Negative control (PRP alone) |
|---|---|---|---|---|---|
| Day 1 | 1.44 | 1.75 | 0.42 | 0.57 | 1.18 |
| P | 0.02 | 0.02 | 0.001 | 0.009 | |
| Day 2 | 1.65 | 2.04 | 1.22 | 1.07 | 1.9 |
| P | 0.104 | 0.314 | 0.039 | 0.069 | |
| Day 5 | 1.95 | 1.96 | 0.82 | 0.5 | 0.42 |
| P | 0.036 | 0.032 | 0.144 | 0.65 | |
| Day 7 | 0.99 | 1.25 | 0.11 | 0.5 | 0.54 |
| P | 0.068 | 0.071 | 0.02 | 0.008 | |
| Day 10 | 0.85 | 1.34 | 0 | 0.49 | 0.3 |
| P | 0.084 | 0.04 | 0.047 | 0.103 | |
| Day 14 | 0.68 | 1.68 | 0 | 0.51 | 0.34 |
| P | 0.015 | 0.069 | 0.026 | 0.04 | |

P values are difference in concentration with respect to the negative control group.

The compositions prepared in Example 1 and Comparative Example 3 secreted significantly more platelet-derived growth factor for a long period of time (1-14 days) with respect to the negative control group. They secreted platelet-derived growth factor at higher concentration than the negative control group thereafter.

In contrast, the compositions prepared in Comparative Examples 14 and 13, wherein batroxobin and tranexamic acid were not mixed, secreted remarkably less plateletmL of 2% fetal bovine serum was used. The culture medium was replaced once in three days. The proliferation of stem cells was measured on days 2, 5, 7 and 14 by WST colorimetric assay (EZ-Cytox, Daeillab Service). All experiments were repeated 3 times and the result is shown in Table 5.

The data shown in Table 5 represent fold change with respect to the value for the positive control group measured on day 0.

TABLE 5

| Fold change | Day 0 | Day 2 | P | Day 5 | P | Day 7 | P | Day 14 | P |
|---|---|---|---|---|---|---|---|---|---|
| Positive control (2% FBS) | 1.00 | 1.33 | | 2.47 | | 3.19 | | 5.84 | |
| Negative control (PRP alone) | 1.00 | 0.91 | 0.002 | 2.29 | 0.583 | 3.30 | 0.787 | 5.97 | 0.837 |
| Ex. 1 (PRP + Ca + BTX + TXA) | 1.00 | 1.46 | 0.251 | 4.20 | 0.000 | 6.11 | 0.000 | 8.26 | 0.028 |
| Ex. 2 (PRP + Ca + BTX + TXA) | 1.00 | 1.37 | 0.555 | 3.63 | 0.000 | 4.78 | 0.002 | 6.98 | 0.110 |
| Ex. 3 (PRP + Ca + BTX + TXA) | 1.00 | 1.38 | 0.528 | 3.84 | 0.000 | 4.68 | 0.009 | 7.23 | 0.095 |
| Comp. Ex. 3 (PRP + Ca + BTX) | 1.00 | 1.45 | 0.246 | 4.08 | 0.000 | 5.42 | 0.000 | 7.92 | 0.024 |
| Comp. Ex. 4 (PRP + Ca + BTX) | 1.00 | 1.42 | 0.349 | 3.76 | 0.000 | 4.67 | 0.000 | 6.87 | 0.130 |
| Comp. Ex. 6 (PRP + Ca + BTX) | 1.00 | 1.32 | 0.943 | 3.68 | 0.000 | 4.37 | 0.002 | 7.15 | 0.092 |
| Comp. Ex. 13 (PRP + Ca) | 1.00 | 1.33 | 0.786 | 3.66 | 0.001 | 3.93 | 0.016 | 7.54 | 0.049 |
| Comp. Ex. 14 (PRP + Ca + TXA) | 1.00 | 1.39 | 0.381 | 3.70 | 0.000 | 5.16 | 0.000 | 7.66 | 0.011 |
| Comp. Ex. 15 (PRP + Ca + THRB) | 1.00 | 1.40 | 0.307 | 4.11 | 0.000 | 4.48 | 0.001 | 6.57 | 0.612 |
| Comp. Ex. 17 (PRP + hyaluronic acid) | 1.00 | 1.27 | 0.281 | 2.50 | 0.729 | 3.41 | 0.032 | 5.85 | 0.984 |
| Comp. Ex. 18 (PRP + Ca + hyaluronic acid) | 1.00 | 1.34 | 0.793 | 2.92 | 0.015 | 4.01 | 0.005 | 6.45 | 0.416 | derived growth factor with respect to the negative control group. Especially, the secretion amount was decreased rapidly from day 7, and undetectable or very trace amount was detected from day 10.

<Experimental Example 4> Proliferation Ability of Stem Cells

From among the compositions tested in Experimental Example 2, stem cell proliferation ability was compared for the compositions exhibiting short gelation time and contraction time and enough gelation (Examples 1-3, Comparative Examples 3-4, 6, 13-15, 17 and 18). The compositions not exhibiting gelation were excluded because they are not retained at the lesion site after being injected into the body but are absorbed, degraded or lost.

The proliferation ability of stem cells was analyzed as follows. First, after seeding bone marrow-derived stem cells onto a 24-well culture plate with a density of $5 \times 10^2$ cells/cm$^2$, the cells were cultured for 24 hours in LG DMEM containing 10% fetal bovine serum and an antibiotic (Hy-Clone, Thermo Fisher Scientific Inc., Waltham, MA, USA). After preparing compositions as in Examples 1-3 and Comparative Examples 3-4, 6, 13-15, 17 and 18 by washing out, the cells were treated with each composition with a volume of 10% of the medium at different time points. When treating the composition, LG DMEM containing 2% fetal bovine serum and an antibiotic was used. As a negative control group, 2 mL of the platelet-rich plasma prepared in Preparation Example 1 was used. As a positive control group, 2

As shown in Table 5, whereas the positive control group showed values of 1.33 or higher from day 2, the negative control group to which only the platelet-rich plasma was administered alone showed decreased proliferation of stem cells from day 2, which was increased from day 5.

The compositions of Comparative Examples 18 and 19 wherein hyaluronic acid and calcium were added showed significantly lower stem cell proliferation as compared to the negative control group.

The compositions prepared in Examples 1-3 showed significantly increased stem cell proliferation as compared to the positive control group and the negative control group. In particular, the composition of Example 1 wherein the mixing volume ratio of batroxobin and calcium was 2:1 showed the most increased stem cell proliferation. Specifically, the composition of Example 1 showed 1.7-fold increase on day 5, 1.92-fold increase on day 7 and 1.36-fold increase on day 14.

The compositions of Comparative Examples 3, 4 and 6, wherein tranexamic acid was excluded unlike the compositions of Examples 1-3, showed significantly lower stem cell proliferation ability as compared to the respective examples with the same mixing ratios.

That is to say, whereas the compositions containing calcium and batroxobin or calcium and tranexamic acid were confirmed to have higher stem cell proliferation ability as compared to the control groups and, it was confirmed that stem cell proliferation ability was decreased when mixed with hyaluronic acid or thrombin even when calcium was present.

In addition, it can be seen that the best effect was achieved when the mixing volume ratio of calcium and batroxobin or tranexamic acid was 1:2. In particular, among the compositions wherein calcium and batroxobin were mixed at a ratio of 1:2, 2:2 and 1:4, the compositions with a mixing ratio of 1:2 (Example 1 and Comparative Example 3) showed the most excellent effect. Since the same result was observed for the example and the comparative example, it can be seen that the best mixing volume ratio of calcium and batroxobin for achieving superior stem cell proliferation effect is 1:2.

<Experimental Example 6> Analysis of Effect of Proliferating Endogenous Stem Cells of Intraosseous Administration 1) Clinical Experiment (Administration into Proximal Humerus)

It was investigated whether the composition containing platelet-rich plasma, calcium, batroxobin and tranexamic acid prepared in Example 1 can enhance the proliferation and function of endogenous cells in bone marrow by administering into the proximal humerus. For this, the proliferation ability of bone marrow stem cells was investigated as follows. First, a patient scheduled to receive proximal humerus surgery within 3-14 days was seated on a chair. After slightly rotating the humerus internally toward the abdomen, the injection site and an ultrasonic transducer were sterilized with betadine solution, etc. After applying the sterilized gel onto the transducer, it was placed on the proximal humerus and the visibility of the greater tubercle was ensured. After perforating the cortical bone, an 18 G spinal needle was inserted into the proximal humerus. First, about 4-5 mL of bone marrow was extracted to prepare a space into which about 2-5 mL of the composition prepared in Example 1 can be injected. The bone marrow extracted from the lesion site before the injection of the composition of Example 1 was used as a control group.

2) Colony-Forming Unit-Fibroblast (CFU-F) Assay

The effect of enhancing the proliferation and function of the bone marrow stem cells extracted from the patient was analyzed by colony-forming unit-fibroblast assay.

The colony-forming unit-fibroblast assay was conducted as follows. First, bone marrow was extracted from the lesion site prior to the administration of the composition of Example 1 (control group). Then, 3-7 days after administration to the lesion site, bone marrow was extracted from the lesion site (test group) and a normal site (comparison group). Bone marrow mononuclear cells were isolated from the bone marrow and seeded onto a 6-well culture plate at a density of $2\times10^4$ cells/cm$^2$ (FIG. 1, Table 6) and $1\times10^5$ cells/cm$^2$ (FIG. 2, Table 7, P0), respectively. CFU-F assay was conducted 14 days later without subculturing. FIG. 3 (Table 7, P1) shows a result of subculturing once, seeding onto a 6-well culture plate at a density of $1\times10^2$ cells/cm$^2$ and then conducting CFU-F assay 14 days later.

The CFU-F assay was conducted as follows. The cells were washed with DPBS (Dulbecco's phosphate-buffered saline), fixed with 4% paraformaldehyde and then stained with 0.1% crystal violet solution for 1 hour. After the staining was completed, a cell colony was observed after washing with running water. A cell colony of 50 or more fibroblasts was defined as a fibroblast colony-forming unit, and the number and size of fibroblast colony-forming units were measured. The result is shown in Table 6 and FIG. 1. Data were presented as mean±standard deviation.

FIG. 1 shows the colony-forming unit-fibroblast (CFU-F) assay result for the bone marrow extracted from the patient before and after the administration of the composition prepared in Example 1.

TABLE 6

| | Control group (affected before injection) | Comparison group (contralateral normal w/o PRP injection) | Test group (affected w/PRP injection) | P value |
|---|---|---|---|---|
| Number | 11.33 ± 4.16 | 14.66 ± 3.51 | 32.33 ± 1.15 | 0.007 |
| Size (mm$^2$) | 4.42 ± 0.56 | 5.37 ± 0.72 | 8.49 ± 0.75 | 0.001 |

As shown in Table 6, the average frequency of fibroblast colony-forming units was 14.66 (1 out of 1,364.3 bone marrow stem cells) before the injection of the composition according to the present disclosure (Example 1) to the proximal humerus. In contrast, the average frequency was increased 2.2-fold to 32.33 (1 out of 618.6 bone marrow stem cells) after the injection of the composition prepared in Example 1. The comparison group showed a frequency of 11.33 (1 out of 1,765.2 bone marrow stem cells), which was similar to that of the control group.

The size of the fibroblast colony-forming unit was 5.37±0.72 mm² for the control group, and was increased 1.58-fold to 8.49±0.75 mm² in the test group. The size of the comparison group was 4.42±0.56 mm², which was similar to that of the control group (P=0.238).

Figure 2:
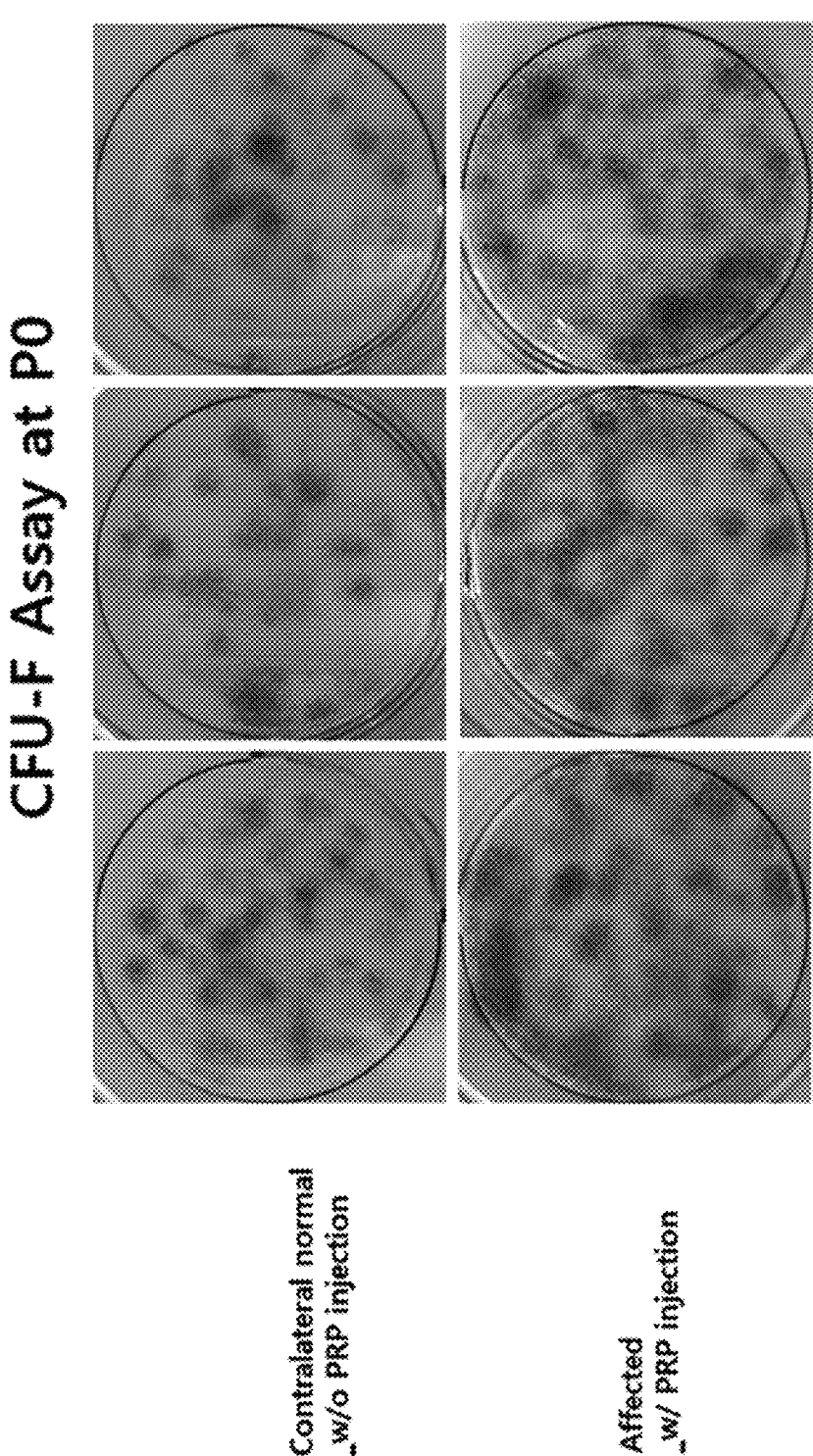
FIG. 2 shows the result of colony-forming unit-fibroblast (CFU-F) assay for cells isolated from bone marrow taken from a patient prior to subculturing (P0) before and after the administration of a composition prepared in Example 1
Figure 3:
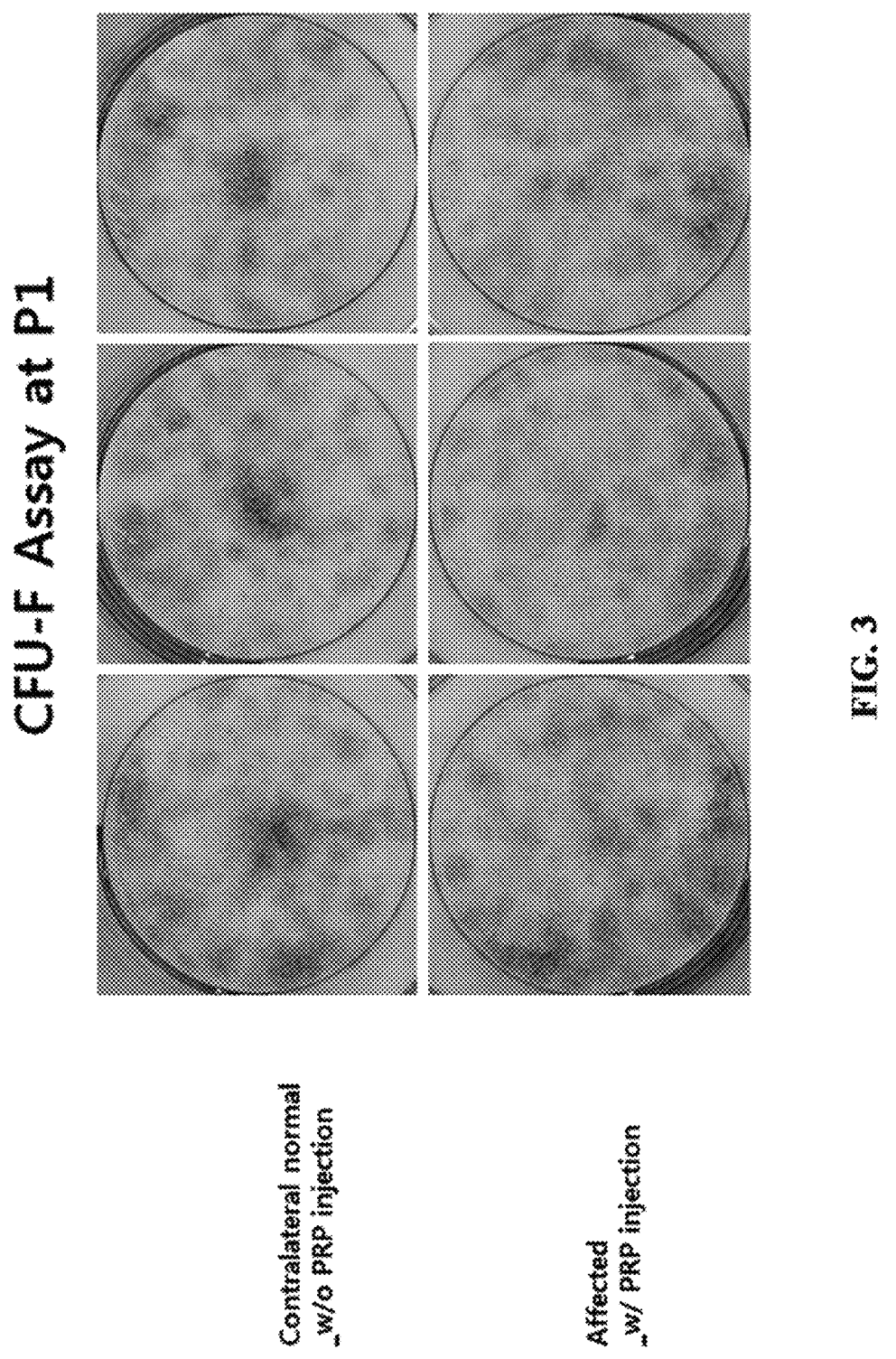

<Experimental Example 7> Analysis of Effect of Proliferating Endogenous Cells Depending on Subculturing of Bone Marrow Stem Cells In order to investigate the effect of the composition prepared in Example 1 over a generation of the bone marrow stem cells, colony-forming unit-fibroblast assay was conducted before (P0) and after (P1) subculturing according to the method of Experimental Example 6, and the result is shown in Table 7 and FIGS. 2 and 3. Data were presented as mean±standard deviation. The bone marrow stem cells before subculturing were represented by P0, and the subcultured bone marrow stem cells were represented by P1.

FIG. 2 shows the colony-forming unit-fibroblast (CFU-F) assay result for the bone marrow extracted from the patient prior to subculturing (P0) before and after the administration of the composition of Example 1, and FIG. 3 shows the colony-forming unit-fibroblast (CFU-F) assay result for the bone marrow extracted from the patient after subculturing (P1) before and after the administration of the composition of Example 1.

TABLE 7

| | | Before administration of composition of Example 1 (−) | After administration of composition of Example 1 (+) | P value |
|---|---|---|---|---|
| P0 | Number | 39.67 ± 6.11 | 71.67 ± 3.21 | 0.016 |
| P0 | Size (mm²) | 5.24 ± 0.34 | 8.29 ± 0.63 | 0.013 |
| P1 | Number | 60.33 ± 5.51 | 73.33 ± 4.04 | 0.014 |
| P1 | Size (mm²) | 5.45 ± 0.92 | 6.39 ± 0.61 | 0.256 |

As shown in Table 7, the average frequency of fibroblast colony-forming units prior to subculturing (P0) before and after the administration of the composition of Example 1 was 39.67 (1/2,520.8 bone marrow stem cells) and 71.67 (1 out of 1,395.3 bone marrow stem cells), respectively. The average frequency was increased 1.81-fold after the administration.

The average frequency of fibroblast colony-forming units after subculturing (P1) before and after the administration of the composition of Example 1 was 60.33 (1 out of 1.66 bone marrow stem cells) and 73.33 (1 out of 1.36 bone marrow stem cells), respectively. The average frequency was increased 1.22-fold after the administration.

The size of the fibroblast colony-forming units was also increased 1.58-fold after the administration of the composition of Example 1. Through this, it can be seen that the administration of the composition of Example 1 according to the present disclosure into bone marrow is effective in enhancing the proliferation and function of endogenous cells in the bone marrow. It was confirmed that this effect is sustained after subculturing. That is to say, it can be seen that the composition of the present disclosure of Example 1 exhibits effect for the endogenous cells in the long term.

<Experimental Example 7> Clinical Experiment

The effect of the injection of the composition of Example 1 in humeral bone marrow prior to treatment of a rotator cuff disease on the result of rotator cuff repair was investigated.
1) Rotator Cuff Repair Using Multiple Channeling Rotator cuff repair was performed on the lateral decubitus under general anesthesia. It was performed on a patient with a rotator cuff disease, and the composition of Example 1 was injected into the caput and metaphysis of the affected humerus 5 days before the rotator cuff repair. The rotator cuff repair was performed by conducting multiple channeling on the rotator cuff attachment site so as to facilitate the access of the bone marrow stem cells of the caput and the metaphysis to the rotator cuff attachment site.

Specifically, systematic exploratory arthroscopy was performed on the glenohumeral joint and the subacromial space, and appropriate treatment was made if necessary. After removing the worn-out portion of the rotator cuff, tear size, the number of affected tendons and visual tendon grade were recorded. If the excursion of torn tendon was not large, superior capsulotomy, coracohumeral ligament release and tendon mobilization including medialization of the supraspinatus insertion, etc. were conducted. At the rotator cuff attachment site of the greater tubercle, the soft tissue was removed and the removal of the calcified fibrocartilage layer was performed at a minimum.

Figure 4:
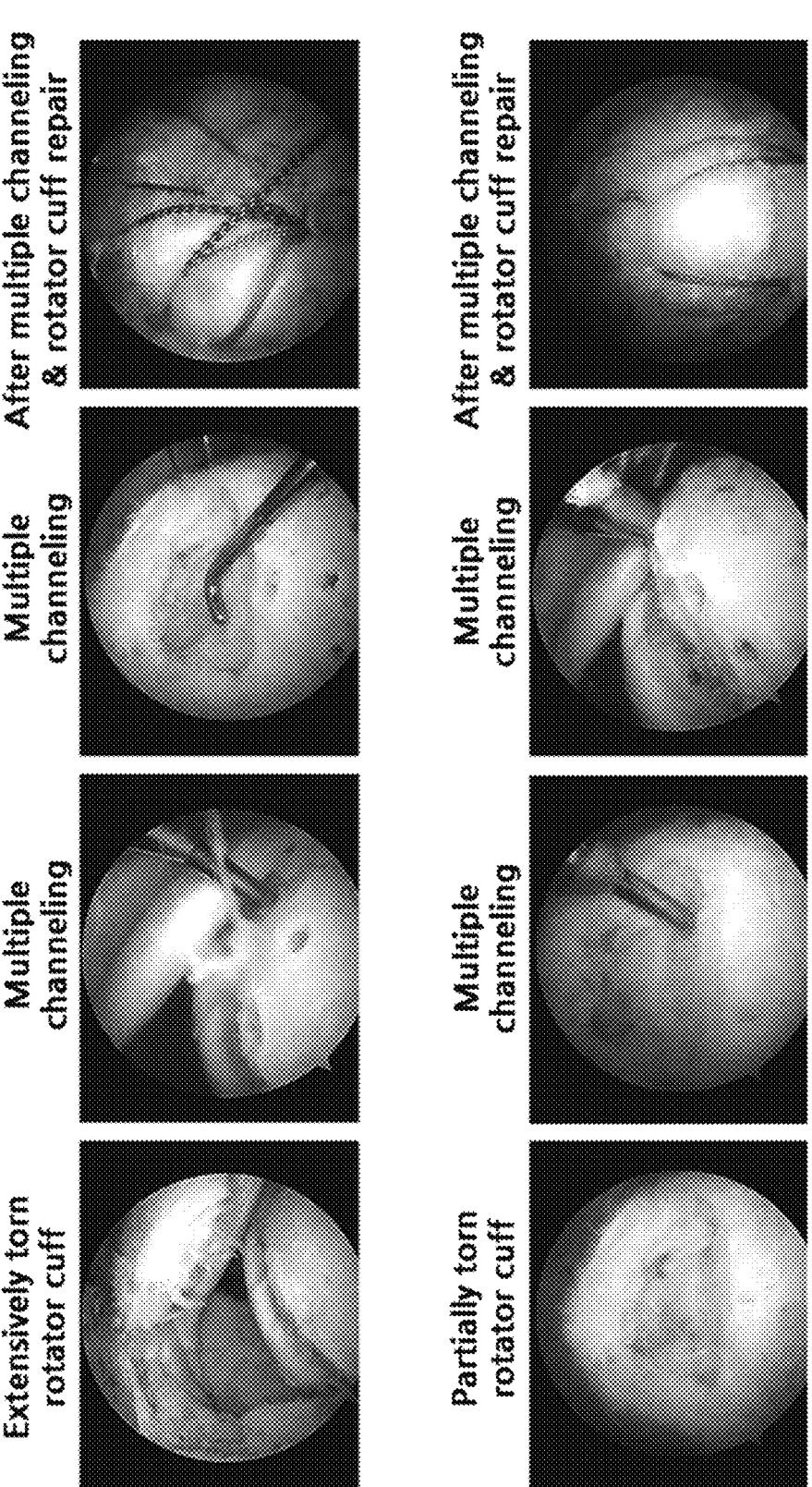
FIG. 4 shows a surgical procedure of rotator cuff repair through multiple channeling using a composition of Example 1.

A communication route between the bone marrow of the proximal humerus and the rotator cuff attachment site was prepared by multiple channeling which is a type of bone marrow stimulation procedure. The multiple channeling was performed around the greater tubercle of the proximal humerus using the previously reported method. A passage through which the medullary cavity of the humerus and the rotator cuff attachment site in the greater tubercle can be connected was prepared by perforating several channels from the joint-cartilage boundary of the greater tubercle to the outer ridge using a bone punch with a diameter of 1.9-2.1 mm. It is recommended to use a long and thin punch rather than a short and thick one because the communication route can be formed more surely and the risk of fracture is decreased. The channeling is applicable not only to the greater tubercle which rotates the humerus internally and externally but also to the part requiring healing and regeneration. In general, the distance between the channels is about 4-5 mm and the channel depth is 10 mm or greater. Floating of marrow droplets from bone marrow through the channels could be observed. After the multiple channeling, rotator cuff repair was performed. The surgical procedures are illustrated in FIG. 4.
2) Evaluation of Clinical and Structural Results For evaluation of clinical and structural results, immune response-related symptoms and signs such as fever, chill, pruritus, dyspnea, urticaria, rash, etc. were observed. Also, erythema, swelling, abnormal discharge, etc. at the injection site were observed.

The clinical status of the patient was analyzed using the standardized evaluation results before and 3, 6 and 12 months after the treatment. The result was evaluated based on (1) pain, (2) range of joint motion, (3) muscular power, and (4) commonly used six shoulder joint functional scores.

3) Statistical Analysis

Nominal values and ordinal values were tested by Pearson's chi-squared test. Scale values were compared by independent t-test. The pain, range of joint motion, muscular power and functional scores before and after the treatment were analyzed by analysis of covariance in consideration of the status prior to the surgery. P<0.05 was considered as statistically significant.

4) Demographic Characteristics of Patients

The demographic characteristics of the patients who participated in the experiment are summarized in Table 8.

TABLE 8

| Parameters | 8 in total |
|---|---|
| Average age (years) | 60.1 ± 11.3 |
| Sex (male:female) | 5:3 |
| Hand dominance (yes:no) | 4:4 |
| Duration of symptom manifestation (months) | 20.6 ± 28.5 |
| Duration of symptom aggravation (months) | 2.6 ± 2.5 |
| Cofield type (partial:small:medium:large:extensive) | 3:0:1:3:1 |
| Boileau type (partial:I:I:II:IV) | 3:1:0:1:3 |
| Row 1:row 2 | 2:6 |
| Acromioplasty (yes:no) | 4:4 |

As shown in Table 8, eight patients participated in the clinical evaluation. Magnetic resonance imaging was performed on 6 patients (75%). The average age of the patients was 60 years. Five were male and three were female. The average duration of symptoms was 20 months. Three patients had partial rotator cuff tear, and five had overall tear (The number of patients with medium, large and extensive tear was 1, 3 and 1, respectively).

Clinical experiment was conducted on the eight patients and they were monitored for 12 months or longer after surgery. During the period, no abnormal response was observed systemically or locally after the administration of the composition prepared in Example 1 of the present disclosure.

5) Pain Analysis

Pain was measured after performing multiple channeling and rotator cuff repair by administrating the composition prepared in Example 1 of the present disclosure. Specifically, pain during rest and movement and nighttime pain were evaluated using a 10-cm visual analog scale. Average pain score was calculated by averaging the three pain scores. Additionally, worst pain score was measured. The result is shown in Table 9.

TABLE 9

| Parameters | | Before treatment | 3 months | 6 months | 1 year |
|---|---|---|---|---|---|
| Pain during rest | Value | 3.25 ± 1.75 | 3.63 ± 2.56 | 2.00 ± 1.83 | 0.00 ± 0.00 |
| | P value | — | 0.670 | 0.025 | 0.046 |
| Pain during movement | Value | 5.07 ± 1.29 | 5.38 ± 2.04 | 3.04 ± 2.22 | 0.08 ± 0.17 |
| | P value | — | 0.933 | 0.072 | 0.001 |
| Nighttime pain | Value | 4.88 ± 2.23 | 4.50 ± 1.41 | 2.57 ± 2.76 | 0.25 ± 0.50 |
| | P value | — | 0.685 | 0.052 | 0.010 |
| Average pain | Value | 4.37 ± 1.56 | 4.50 ± 1.75 | 2.54 ± 2.23 | 0.11 ± 0.22 |
| | P value | — | 0.869 | 0.042 | 0.008 |
| Worst pain | Value | 6.13 ± 1.73 | 5.88 ± 2.03 | 3.86 ± 2.54 | 0.25 ± 0.50 |
| | P value | — | 0.749 | 0.028 | 0.007 |

As shown in Table 9, when multiple channeling and rotator cuff repair were performed by administering the composition of Example 1 according to the present disclosure, all the pain scores were significantly decreased gradually as compared to before the surgery. In particular, one year after the surgery, pain during rest, pain during movement, nighttime pain, average pain and worst pain disappeared or were decreased remarkably by 10-20 times or more.

6) Analysis of Range of Joint Motion

The range of joint motion was measured using a protractor. Active forward flexion, abduction, external rotation and internal rotation were measured. The muscular power of supraspinatus muscle, infraspinatus muscle and subscapularis muscle was measured using an electronic device (CHS, CAS, Korea). The result is shown in Table 10.

TABLE 10

| Parameters | | Before treatment | 3 months | 6 months | 1 year |
|---|---|---|---|---|---|
| Forward | Value | 135.62 ± 45.85 | 115.63 ± 36.30 | 143.57 ± 17.01 | 156.25 ± 14.93 |
| flexion, ° | P value | — | 0.271 | 0.482 | 0.297 |
| Abduction,° | Value | 140.63 ± 50.46 | 107.50 ± 41.14 | 142.86 ± 25.14 | 163.75 ± 12.50 |
| | P value | — | 0.128 | 0.720 | 0.311 |
| External | Value | 44.38 ± 14.74 | 23.75 ± 13.82 | 30.71 ± 12.05 | 46.25 ± 14.36 |
| rotation,° | P value | — | 0.003 | 0.028 | 1.000 |
| Internal rotation, | Value | 10.00 ± 2.88 | 5.75 ± 3.92 | 7.71 ± 3.50 | 10.25 ± 1.26 |
| vertebral level | P value | — | 0.006 | 0.280 | 0.236 |

As shown in Table 10, forward flexion, abduction, external rotation and internal rotation were not decreased or aggravated as compared to before the surgery.

7) Analysis of Muscular Power

TABLE 11

| Parameters | | Before treatment | 3 months | 6 months | 1 year |
|---|---|---|---|---|---|
| Supraspinatus | Value | 5.50 ± 7.07 | 3.00 ± 3.05 | 8.66 ± 5.58 | 16.00 ± 4.81 |
| muscle, lb | P value | — | 0.463 | 0.360 | 0.178 |
| Infraspinatus | Value | 6.45 ± 3.77 | 5.12 ± 1.49 | 9.83 ± 5.45 | 14.45 ± 4.31 |
| muscle, lb | P value | — | 0.240 | 0.511 | 0.348 |
| Subscapularis | Value | 11.15 ± 6.59 | 9.03 ± 5.17 | 14.20 ± 5.61 | 21.15 ± 0.435 |
| muscle, lb | P value | — | 0.572 | 0.367 | 0.435 |

As shown in Table 11, the average muscular power of supraspinatus muscle was 5.50±7.07 lb before the multiple channeling and rotator cuff repair using the composition of Example 1 according to the present disclosure and it was increased 2.9-fold to 16.00±4.81 lb after the surgery. The average muscular power of infraspinatus muscle was increased 2.2-fold and the average muscular power of subscapularis muscle was increased 1.9-fold. Through this, it can be seen that the administration of the composition prepared in Example 1 of the present disclosure significantly recovers the muscular power of supraspinatus muscle, infraspinatus muscle and subscapularis muscle.

8) Evaluation of Shoulder Joint Function

Shoulder joint function was evaluated based on American Shoulder and Elbow Surgeons (ASES) score, Constant score, UCLA score, Disabilities of the Arm, Shoulder and Hand (DASH) score, and Shoulder Pain and Disability Index (SPADI). The result is shown in Table 12.

TABLE 12

| Parameters | | Before treatment | 3 months | 6 months | 1 year |
|---|---|---|---|---|---|
| American Shoulder and | Value | 50.12 ± 19.12 | 49.38 ± 20.41 | 74.44 ± 21.97 | 96.94 ± 4.19 |
| Elbow Surgeons score | P value | — | 0.674 | 0.032 | 0.018 |
| Constant score | Value | 49.69 ± 19.08 | 40.25 ± 18.19 | 64.66 ± 14.00 | 86.75 ± 7.76 |
| | P value | — | 0.230 | 0.106 | 0.049 |
| UCLA score | Value | 17.13 ± 5.089 | 18.75 ± 7.07 | 27.29 ± 5.02 | 34.00 ± 1.41 |
| | P value | — | 0.568 | 0.008 | 0.003 |

TABLE 12-continued

| Parameters | | Before treatment | 3 months | 6 months | 1 year |
|---|---|---|---|---|---|
| Disabilities of the Arm, | Value | 31.67 ± 13.07 | 41.15 ± 19.21 | 18.45 ± 15.51 | 0.83 ± 1.67 |
| Shoulder and Hand score | P value | — | 0.142 | 0.030 | 0.009 |
| Shoulder Pain and | Value | 45.34 ± 19.81 | 50.19 ± 19.62 | 25.28 ± 22.09 | 1.69 ± 2.89 |
| Disability Index | P value | — | 0.611 | 0.045 | 0.013 |

As shown in Table 12, it was confirmed that the multiple channeling and rotator cuff repair by administering the composition of Example 1 according to the present disclosure significantly increased shoulder joint functions (American Shoulder and Elbow Surgeons (ASES) score, Constant score, UCLA score, Disabilities of the Arm, Shoulder and Hand (DASH) score and Shoulder Pain and Disability Index (SPADI)).

9) Evaluation of Structural Integrity

For evaluation of structural integrity, magnetic resonance imaging (Achieva 3.0 T, Philips Medical System, The Netherlands) was performed 12 months after the surgery. Structural integrity was evaluated using Sugaya et al.'s classification system. Sugaya types 1-3 were considered as healing, and types 4-5 were considered as retare. The result is shown in Table 13.

Figure 5A:
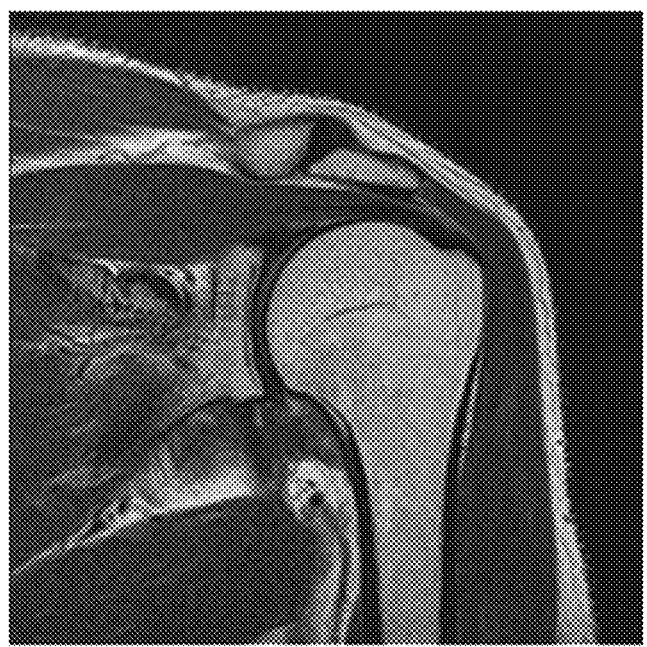
FIG. 5A shows the rotator cuff magnetic resonance image (MRI) of a normal patient.
Figure 5B:
FIG. 5B shows the rotator cuff magnetic resonance image (MRI) of a patient before performing rotator cuff repair through multiple channeling using a composition of Example 1 according to the present disclosure, wherein the red arrow indicates a region where the rotator cuff is not observed due to rotator cuff tear.
Figure 5C:
FIG. 5C shows the rotator cuff magnetic resonance image (MRI) of a patient immediately after performing rotator cuff repair through multiple channeling using a composition of Example 1 according to the present disclosure, wherein the red arrow indicates a passage of a surgical site formed by multiple channeling.
Figure 5D:
FIG. 5D shows the rotator cuff magnetic resonance image (MRI) of a patient one year after performing rotator cuff repair through multiple channeling using a composition of Example 1 according to the present disclosure, wherein the red arrow indicates regenerated rotator cuff.

FIG. 5A shows the rotator cuff magnetic resonance image (MRI) of a normal patient, FIG. 5B shows the rotator cuff magnetic resonance image (MRI) of a patient before performing rotator cuff repair through multiple channeling using a composition of Example 1 according to the present disclosure, wherein the red arrow indicates a region where the rotator cuff is not observed due to rotator cuff tear, FIG. 5C shows the rotator cuff magnetic resonance image (MRI) of a patient immediately after performing rotator cuff repair through multiple channeling using a composition of Example 1 according to the present disclosure, wherein the red arrow indicates a passage of a surgical site formed by multiple channeling, and FIG. 5D shows the rotator cuff magnetic resonance image (MRI) of a patient one year after performing rotator cuff repair through multiple channeling using a composition of Example 1 according to the present disclosure, wherein the red arrow indicates regenerated rotator cuff.

TABLE 13

| | Healing | Retare |
|---|---|---|
| Number | 5 | 1 |
| Percentage | 83.3% | 16.7% |

As shown in FIGS. 5A to 5D and Table 13, rotator cuff was healed in five out of the six patients who received multiple channeling and rotator cuff repair using the composition of Example 1 one year later (83.3%).

Specifically, the composition prepared in Example 1 was injected to the proximal humerus by multiple channeling, which is one of bone marrow stimulating procedures, about 3-14 days prior to surgery. One year later, it was confirmed that the rotator cuff was healed completely not only for medium-sized tear but also extensive tear. In particular, regenerated rotator cuff tissue was observed even though the extensively torn rotator cuff was not healed completely due to insufficient mobility of the torn end.

10) Evaluation of Status of Rotator Cuff Muscle

The muscular status of rotator was evaluated by measuring fatty infiltration and muscle atrophy in the outermost section where the coracoid process and the scapular spine are in contact in the oblique sagittal T1-weighted magnetic resonance image. The fatty infiltration was evaluated with Goutallier grades, and the muscle atrophy was evaluated using tangent signs and the cross section of the supraspinatus muscle. The result is shown in Table 14.

Figure 6A:
FIG. 6A shows the rotator cuff magnetic resonance image (MRI) of a normal patient.
Figure 6B:
FIG. 6B shows the rotator cuff magnetic resonance image (MRI) of a patient before performing rotator cuff repair through multiple channeling using a composition of Example 1 according to the present disclosure. The rotator cuff was not observed due to rotator cuff tear.
Figure 6C:
FIG. 6C shows the rotator cuff magnetic resonance image (MRI) of a patient one year after performing rotator cuff repair through multiple channeling using a composition of Example 1 according to the present disclosure. It can be seen that the rotator cuff was regenerated.

FIG. 6A shows the rotator cuff magnetic resonance image (MRI) of a normal patient, FIG. 6B shows the rotator cuff magnetic resonance image (MRI) of a patient before performing rotator cuff repair through multiple channeling using a composition of Example 1 according to the present disclosure. The rotator cuff was not observed due to rotator cuff tear, and FIG. 6C shows the rotator cuff magnetic resonance image (MRI) of a patient one year after performing rotator cuff repair through multiple channeling using a composition of Example 1 according to the present disclosure. It can be seen that the rotator cuff was regenerated.

TABLE 14

| Parameters | | Before surgery (%) | | 1 year (%) | | P value |
|---|---|---|---|---|---|---|
| Goutallier_SS | G0 | 3 | 3.90% | 3 | 3.90% | |
| | G1 | 23 | 29.87% | 24 | 31.17% | |
| | G2 | 26 | 33.77% | 35 | 45.45% | |
| | G3 | 8 | 10.39% | 10 | 12.99% | |
| | G4 | 17 | 22.08% | 5 | 6.49% | 0.087 |
| Goutallier_IS | G0 | 8 | 10.39% | 6 | 7.79% | |
| | G1 | 39 | 50.65% | 43 | 55.84% | |
| | G2 | 22 | 28.57% | 21 | 27.27% | |
| | G3 | 3 | 3.90% | 1 | 1.30% | |
| | G4 | 5 | 6.49% | 6 | 7.79% | 0.81 |
| Goutallier_SSC | G0 | 21 | 27.27% | 13 | 16.88% | |
| | G1 | 44 | 57.14% | 45 | 58.44% | |
| | G2 | 9 | 11.69% | 13 | 16.88% | |
| | G3 | 2 | 2.60% | 4 | 5.19% | |
| | G4 | 1 | 1.30% | 2 | 2.60% | 0.46 |
| Tangent | G1 | 41 | 53.25% | 56 | 72.73% | |
| | G2 | 29 | 37.66% | 14 | 18.18% | |
| | G3 | 7 | 9.09% | 7 | 9.09% | 0.023 |
| Occupation ratio | G1 | 29 | 37.66% | 35 | 45.45% | |
| | G2 | 31 | 40.26% | 36 | 46.75% | |
| | G3 | 17 | 22.08% | 6 | 7.79% | 0.045 |

As shown in FIGS. 6A to 6C and Table 14, the fatty infiltration and muscle atrophy of the rotator cuff were improved after the surgery in some patients. The muscle atrophy was evaluated with Goutallier grades. Before the surgery, the Goutallier grades for the supraspinatus muscle, the infraspinatus muscle, the subscapularis muscle, and the teres minor muscle were 3, 2, 1 and 1, respectively. They were improved one year after the surgery to 2, 2, 1 and 1, respectively. As a result of evaluating the muscle atrophy using tangent signs, the muscle atrophy was improved from grade 2 before the surgery to grade 1 one year after the surgery. The cross section of the supraspinatus muscle was improved from 298.9 mm$^2$ prior to the surgery to 326.3 mm$^2$ one year after the surgery.

Through these results, it was confirmed that the composition containing platelet-rich plasma, calcium, batroxobin and tranexamic acid of the present disclosure has an activity of effectively enhancing endogenous cell proliferation in bone marrow in rotator cuff repair and, thus, is useful as a therapeutic agent for treating the injury and disease of the musculoskeletal system such as tendon and ligament.

<Experimental Example 8> Clinical Evaluation Before and After Rotator Cuff Repair Using Multiple Channeling While performing rotator cuff repair on a patient having rotator cuff tear of medium size (FIGS. 7A to 7C) and a patient having rotator cuff tear of massive size (FIGS. 8A to 8C), the effect of multiple channeling for injecting the composition of Example 1 into humeral bone marrow in advance was analyzed.

1) Rotator Cuff Repair Using Multiple Channeling

Rotator cuff repair was performed on the lateral decubitus under general anesthesia. It was performed on a patient with a rotator cuff disease, and rotator cuff repair using multiple channeling was performed as follows. First, systematic exploratory arthroscopy was performed on the glenohumeral joint and the subacromial space, and appropriate treatment was made if necessary. After removing the worn-out portion of the rotator cuff, tear size, the number of affected tendons and visual tendon grade were recorded. If the excursion of torn tendon was not large, superior capsulotomy, coracohumeral ligament release and tendon mobilization including medialization of the supraspinatus insertion, etc. were conducted. At the rotator cuff attachment site of the greater tubercle, the soft tissue was removed and the removal of the calcified fibrocartilage layer was performed at a minimum.

A communication route between the bone marrow of the proximal humerus and the rotator cuff attachment site was prepared by multiple channeling which is a type of bone marrow stimulation procedure. The multiple channeling was performed around the greater tubercle of the proximal humerus using the previously reported method. A passage through which the medullary cavity of the humerus and the rotator cuff attachment site in the greater tubercle can be connected was prepared by perforating several channels from the joint-cartilage boundary of the greater tubercle to the outer ridge using a bone punch with a diameter of 1.9-2.1 mm. It is recommended to use a long and thin punch rather than a short and thick one because the communication route can be formed more surely and the risk of fracture is decreased. The channeling is applicable not only to the greater tubercle which rotates the humerus internally and externally but also to the part requiring healing and regeneration. In general, the distance between the channels is about 4-5 mm and the channel depth is 10 mm or greater. Floating of marrow droplets from bone marrow through the channels could be observed. After injecting the composition of Example 1 through the channels formed by multiple channeling, rotator cuff repair was performed.

2) Clinical Evaluation

Figure 7A:
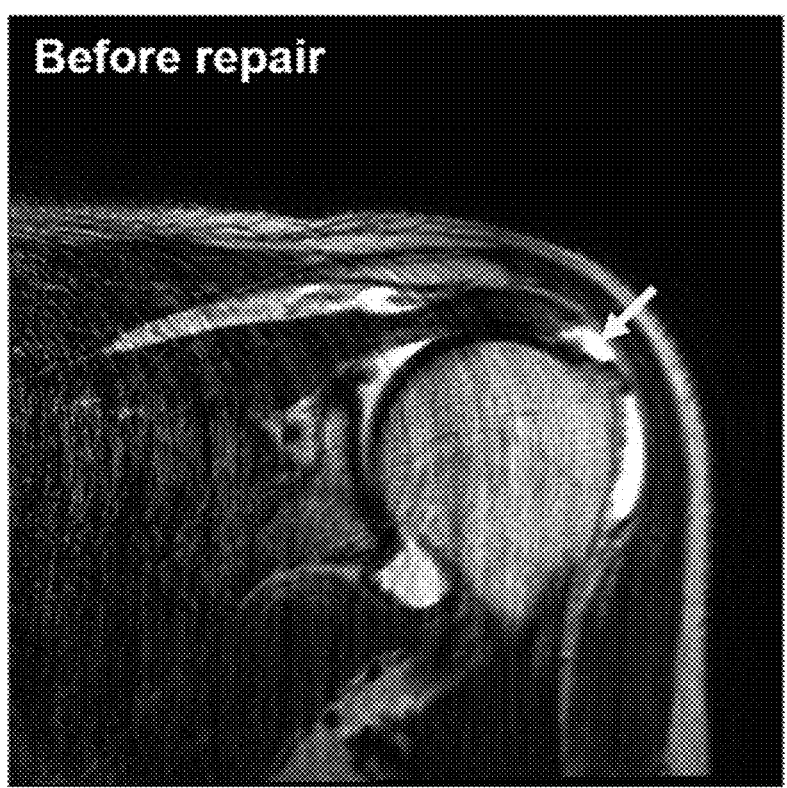
FIG. 7A shows the rotator cuff magnetic resonance image (MRI) of a patient having rotator cuff tear of medium size prior to performing surgery.
Figure 7B:
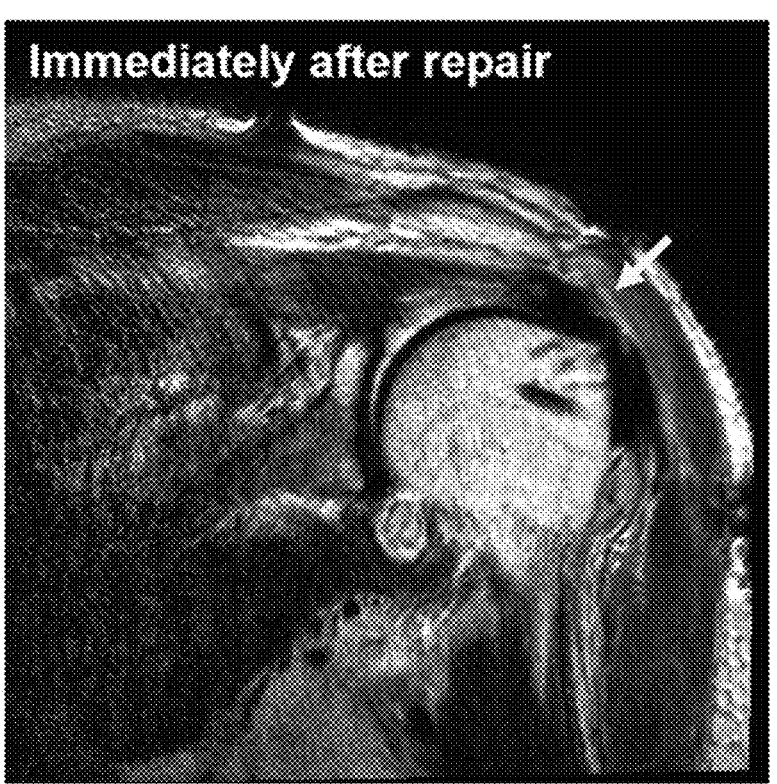
FIG. 7B shows the rotator cuff magnetic resonance image (MRI) of a patient immediately after performing rotator cuff repair through multiple channeling using a composition of Example 1 according to the present disclosure.
Figure 7C:
FIG. 7C shows the rotator cuff magnetic resonance image (MRI) of a patient one year after performing rotator cuff repair through multiple channeling using a composition of Example 1 according to the present disclosure. It can be seen that the rotator cuff was regenerated.

FIG. 7A shows the rotator cuff magnetic resonance image (MRI) of a patient having rotator cuff tear of medium size prior to performing surgery, FIG. 7B shows the rotator cuff magnetic resonance image (MRI) of a patient immediately after performing rotator cuff repair through multiple channeling using a composition of Example 1 according to the present disclosure, and FIG. 7C shows the rotator cuff magnetic resonance image (MRI) of a patient one year after performing rotator cuff repair through multiple channeling using a composition of Example 1 according to the present disclosure. It can be seen that the rotator cuff was regenerated.

Figure 8A:
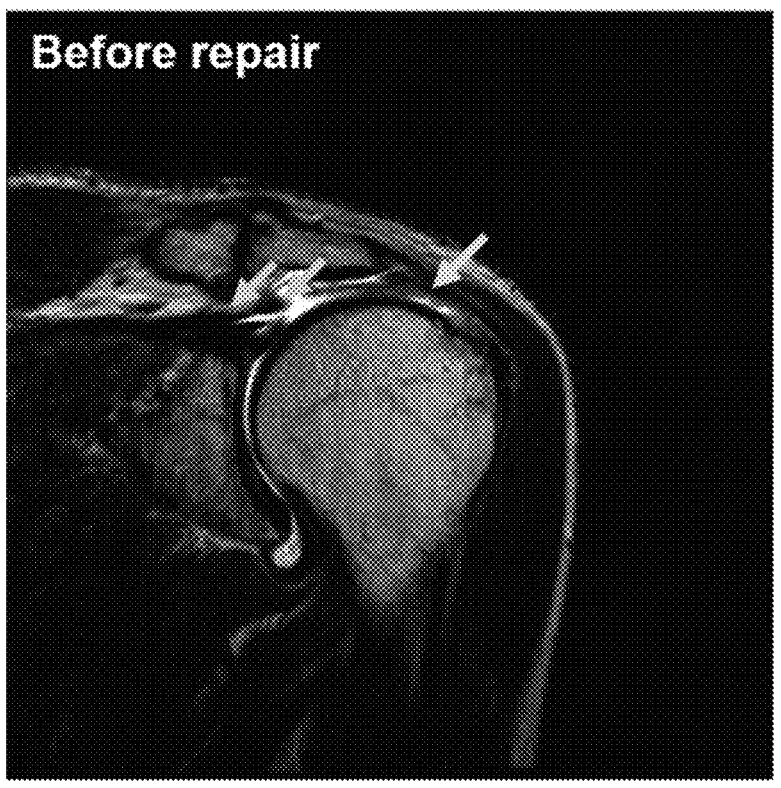
FIG. 8A shows the rotator cuff magnetic resonance image (MRI) of a patient having rotator cuff tear of massive size prior to performing surgery.
Figure 8B:
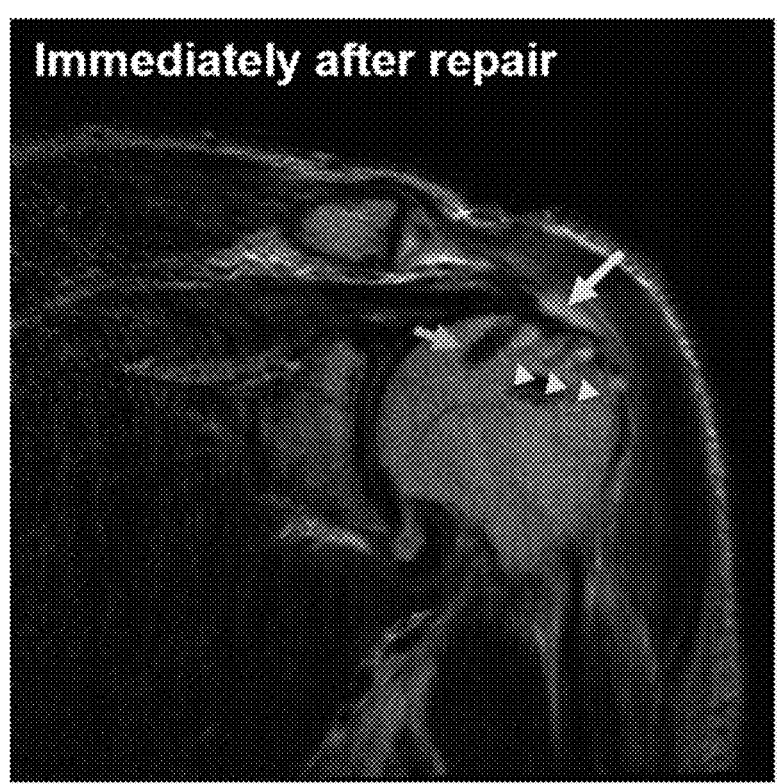
FIG. 8B shows the rotator cuff magnetic resonance image (MRI) of a patient immediately after performing rotator cuff repair through multiple channeling using a composition of Example 1 according to the present disclosure.
Figure 8C:
FIG. 8C shows the rotator cuff magnetic resonance image (MRI) of a patient one year after performing rotator cuff repair through multiple channeling using a composition of Example 1 according to the present disclosure. It can be seen that the rotator cuff was regenerated.

FIG. 8A shows the rotator cuff magnetic resonance image (MRI) of a patient having rotator cuff tear of massive size prior to performing surgery, FIG. 8B shows the rotator cuff magnetic resonance image (MRI) of a patient immediately after performing rotator cuff repair through multiple channeling using a composition of Example 1 according to the present disclosure, FIG. 8C shows the rotator cuff magnetic resonance image (MRI) of a patient one year after performing rotator cuff repair through multiple channeling using a composition of Example 1 according to the present disclosure. It can be seen that the rotator cuff was regenerated.

Figure 9A:
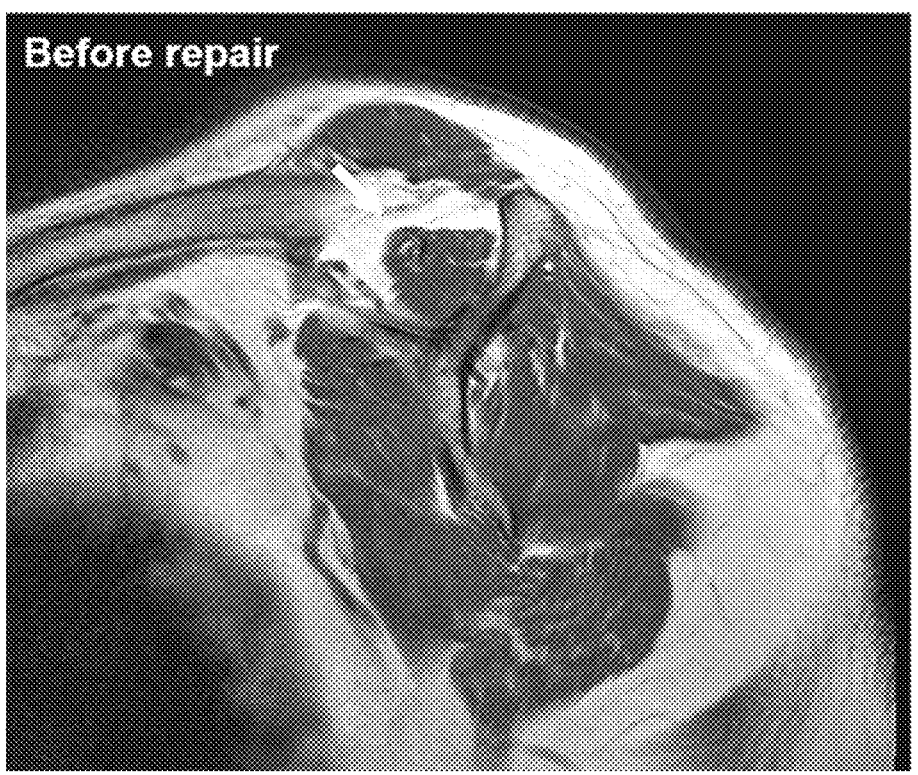
FIG. 9A shows the rotator cuff magnetic resonance image (MRI) of a patient having rotator cuff tear of massive size prior to performing surgery.
Figure 9B:
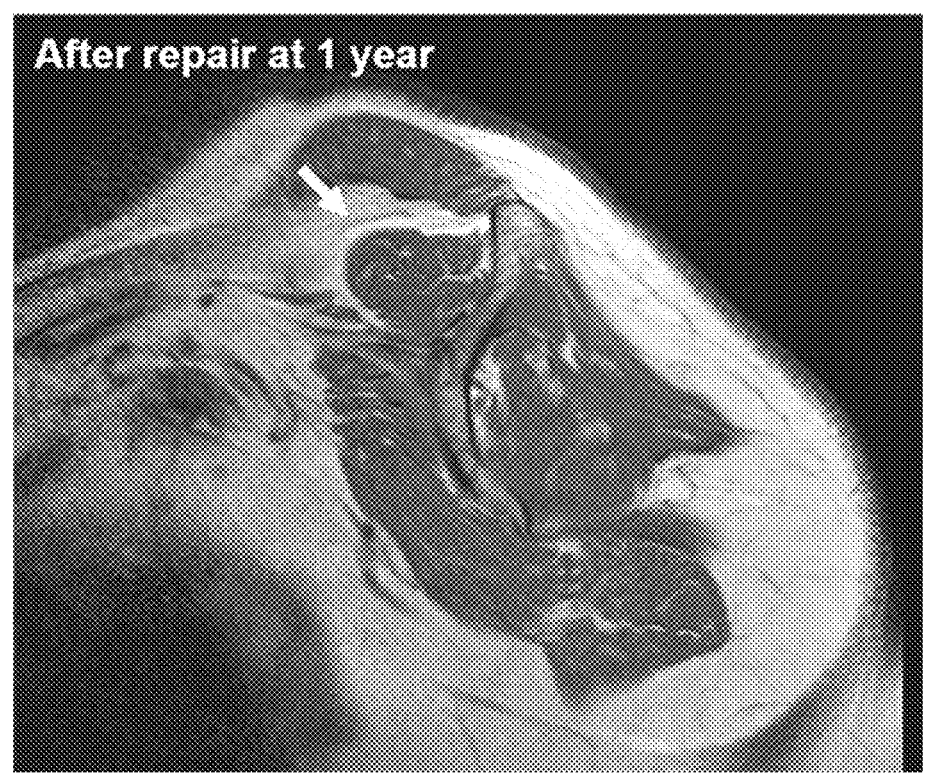
FIG. 9B shows the rotator cuff magnetic resonance image (MRI) of a patient one year after performing rotator cuff repair through multiple channeling using a composition of Example 1 according to the present disclosure. It can be seen that the rotator cuff was regenerated effectively.

FIG. 9A shows the rotator cuff magnetic resonance image (MRI) of a patient having rotator cuff tear of massive size prior to performing surgery, and FIG. 9B shows the rotator cuff magnetic resonance image (MRI) of a patient one year after performing rotator cuff repair through multiple channeling using a composition of Example 1 according to the present disclosure. It can be seen that the rotator cuff was regenerated effectively.

Through these results, it was confirmed that the composition containing platelet-rich plasma, calcium, batroxobin and tranexamic acid of the present disclosure has an effect of increasing the success rate of rotator cuff repair by effectively enhancing the proliferation of endogenous cells in bone marrow. That is to say, it was confirmed that the composition of the present disclosure is effective as a therapeutic agent for treating the injury and disease of the musculoskeletal system such as tendon and ligament and as an adjuvant for musculoskeletal system repair.

<Experimental Example 10> Effect on Chemotaxis of Stem Cells

Figure 10:
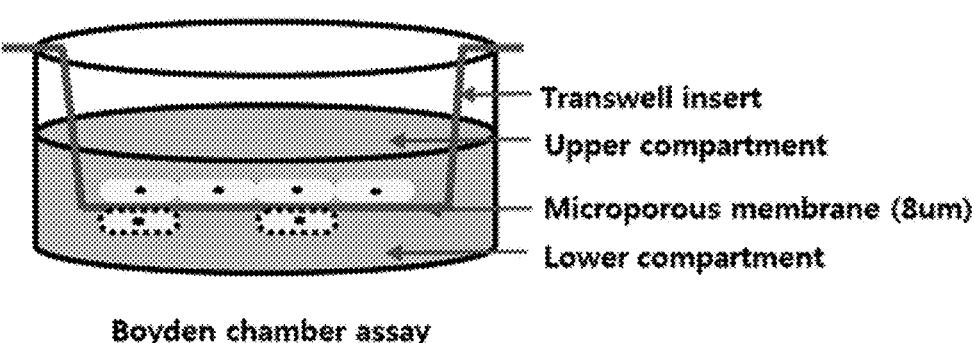
FIG. 10 schematically shows a procedure of measuring the chemotaxis of stem cells by Boyden chamber assay.
Figure 11:
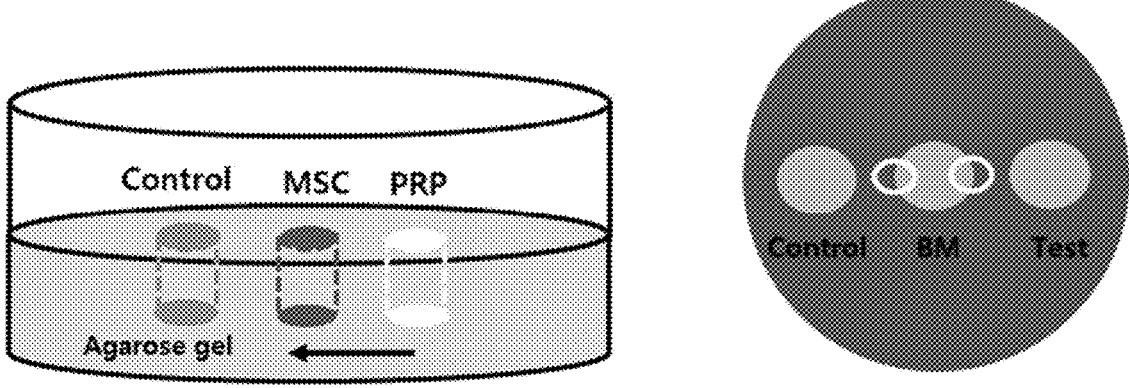
FIG. 11 schematically shows a procedure of measuring the chemotaxis of stem cells by agarose chemotaxis assay.

The effect of the composition prepared in Example 1 on the chemotaxis of stem cells was evaluated with the following two methods. FIG. 10 schematically shows a procedure of measuring the chemotaxis of stem cells by Boyden chamber assay, and FIG. 11 schematically shows a procedure of measuring the chemotaxis of stem cells by agarose chemotaxis assay.

1) Boyden Chamber Assay $1 \times 10^4$ bone marrow stem cells were seeded onto an upper insert of a transwell and cultured for 24 hours in LG DMEM containing an antibiotic (HyClone, Thermo Fisher Scientific Inc., Waltham, MA, USA). 24 hours later, the composition of Example 1 of 10% of the medium volume was treated to the antibiotic-containing DMEM at the bottom by washing out. LG DMEM not containing FBS was used as a negative control group, and G-CSF 100 ng/mL, SDF-1α 100 ng/mL and IL-1β 100 ng/mL were compared as positive control groups of chemotaxis. In order to count the cells that migrated from the insert to the bottom, the cells remaining on the insert was removed 24 hours later and only the cells at the bottom were left. After fixing with 4% paraformaldehyde and staining with crystal violet, the cells were observed under a microscope. For quantification of the cells that migrated to the bottom, $OD_{540}$ was measured after dissolving the crystal violet with acetic acid. The result is shown in Table 15. All experiments were repeated 3 times.

Figure 12:
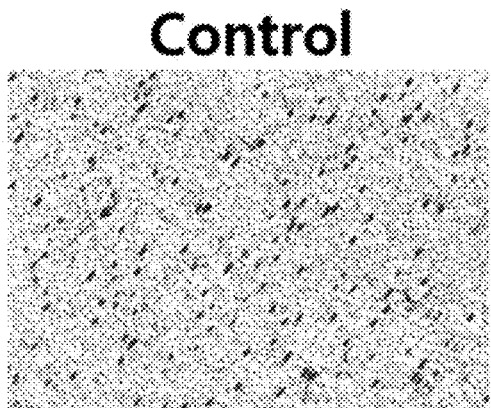
FIG. 12 shows a result of treating stem cells respectively with a composition of Example 1, an antibiotic, G-CSF, SDF-1α or IL-1β and then conducting Boyden chamber assay.
Figure 12:
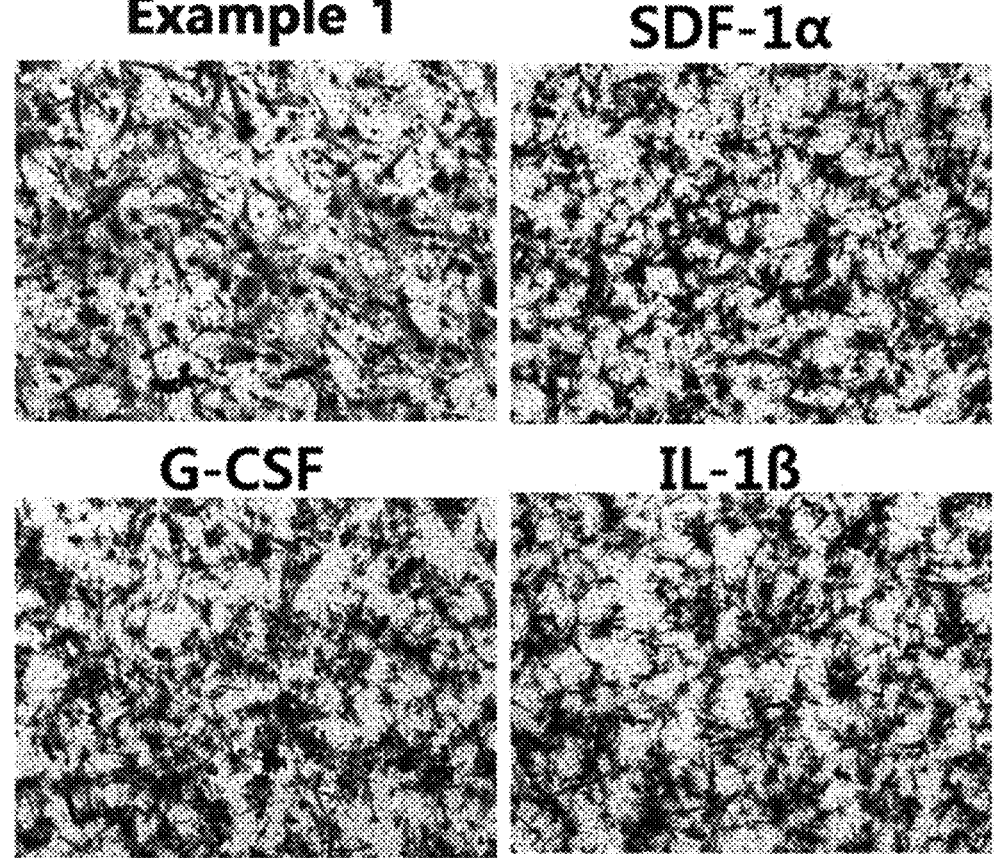

FIG. 12 shows a result of treating stem cells respectively with a composition of Example 1, an antibiotic, G-CSF, SDF-1α or IL-1β and then conducting Boyden chamber assay.

TABLE 15

|  |  | Number of migrated cells | P value |
| --- | --- | --- | --- |
| Control group (antibiotic) |  | 100.00 ± 0.00 | — |
| Example 1 |  | 416.41 ± 226.08 | 0.019 |
| Positive control | G-CSF | 415.01 ± 338.54 | 0.072 |
| groups | SDF-1α | 365.28 ± 280.55 | 0.015 |
|  | IL-1β | 358.85 ± 271.58 | 0.010 |

As shown in FIG. 12 and Table 15, the number of bone marrow stem cells that migrated to the bottom was 4.16 times larger when treated with the composition of Example 1 as compared to the control group (P=0.0187). This result was comparable to or better than that of the positive control groups (4.15 times, 3.65 times and 3.59 times, respectively). That is to say, it can be seen that the composition of the present disclosure (Example 1) exhibits better stem cell-recruiting ability than the positive control groups.

2) Agarose Chemotaxis Assay

First, after preparing 0.8% agarose gel on a 6-well plate, three holes were perforated in each well with intervals of 5 mm using a 5-mm skin biopsy punch. $1\times10^4$ bone marrow stem cells were dispensed into LG DMEM containing 10% FBS and an antibiotic at the center. After waiting for 5 hours until the cells were attached, the medium was replaced with LG DMEM containing the antibiotic only. LG DMEM containing only the antibiotic was added into the left hole as a control group, and the composition of Example 1 of 50% of the volume of the antibiotic-containing DMEM was treated through the right hole by washing out. In addition, G-CSF 100 ng/mL, SDF-1α 100 ng/mL and IL-1β 100 ng/mL were treated for comparison as positive control groups of chemotaxis. 72 hours later, the cells were fixed with 4% paraformaldehyde, stained with DAPI and observed with a fluorescence microscope. The cells that migrated to the left and right sides were imaged with the fluorescence microscope. The number of cells that migrated 100 μm or longer from the end of each hole was counted. The result is shown in Table 16. All experiments were repeated 3 times.

Figure 13:
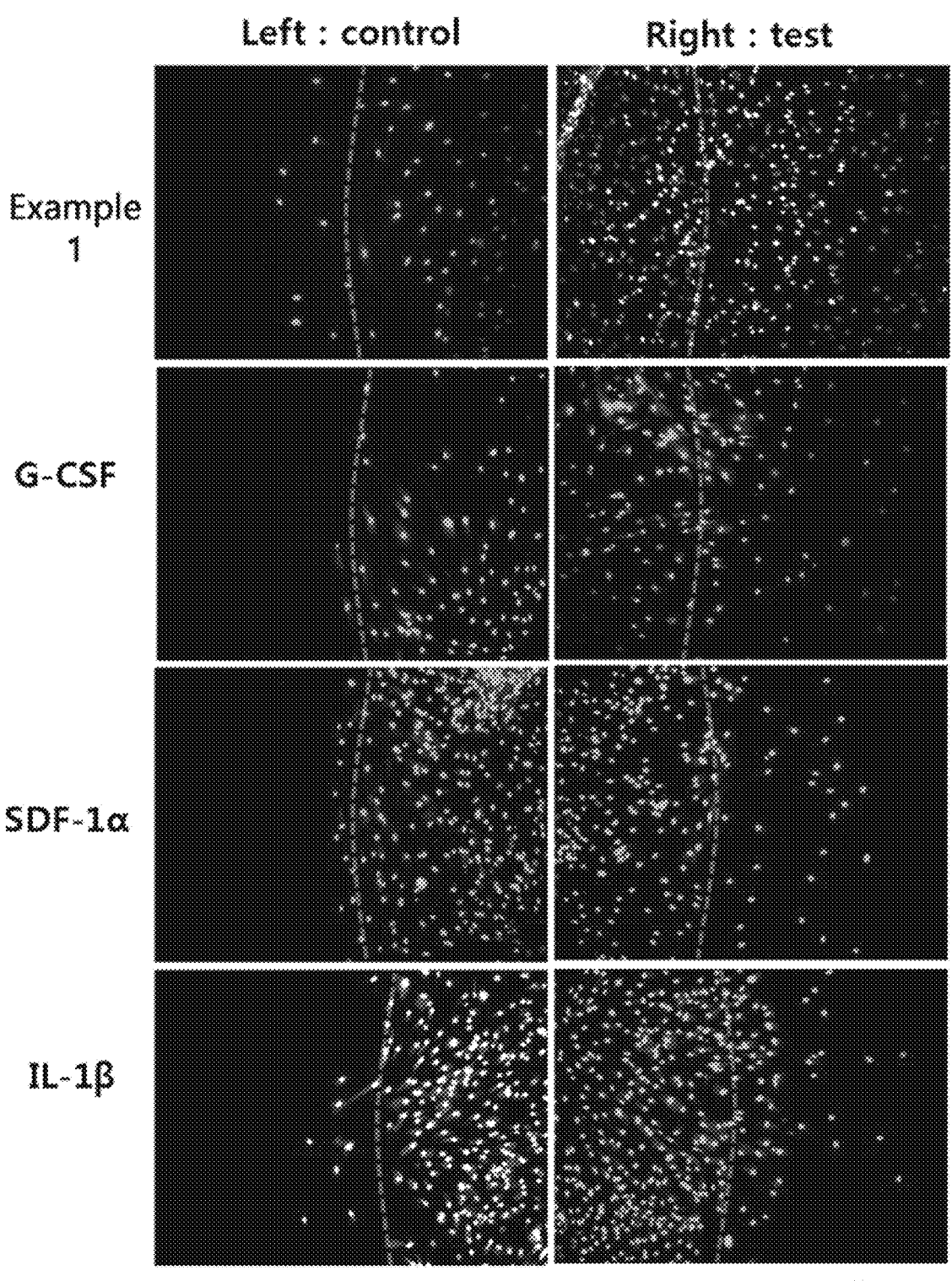
FIG. 13 shows a result of treating stem cells respectively with a composition of Example 1, an antibiotic, G-CSF, SDF-1α or IL-1β and then conducting agarose chemotaxis assay.

FIG. 13 shows a result of treating stem cells respectively with a composition of Example 1, an antibiotic, G-CSF, SDF-1α or IL-1β and then conducting agarose chemotaxis assay.

TABLE 16

|  |  | Number of migrated cells | P value |
| --- | --- | --- | --- |
| Control group (antibiotic) |  | 100.00 ± 0.00 | — |
| Example 1 |  | 935.94 ± 469.63 | 0.000 |
| Positive control groups | G-CSF | 393.76 ± 280.52 | 0.014 |
|  | SDF-1α | 466.68 ± 348.04 | 0.021 |
|  | IL-1β | 314.13 ± 220.72 | 0.063 |

As shown in FIG. 13 and Table 16, 9.36 times more stem cells migrated toward the side treated with the composition of Example 1 as compared to the control group. This result was remarkably superior to that of the positive control groups (3.94 times, 4.67 times and 3.14 times, respectively). That is to say, it can be seen that the composition of the present disclosure (Example 1) has 2 times or higher stem cell-recruiting ability than the positive control groups.

<Experimental Example 11> Effect on Animal Model of Cartilage Defect

1) Animal Model of Cartilage Defect 12-week-old Sprague-Dawley rats (Core Lab Inc., Seoul, Korea) weighing 350 g on average were used as experimental animals. Surgery was performed after anesthetizing the rat. After disinfecting both lower limbs of the rat with betadine solution, the cartilage of the femur was exposed by turning the patella outward by medial approach of the knee joint. An animal model of cartilage defect was prepared by inducing full-thickness cartilage defect of round shape with a diameter 2 mm at a location 2 mm above the intercondylar notch of the trochlear groove using a drill with a diameter of 1 mm.

The animal model of cartilage defect was divided into three groups. Group 1 (damaged group) was a negative control group with full-thickness cartilage damage. Group 2 (microfracture surgery group) received microfracture surgery after full-thickness cartilage damage to induce blood clotting. For group 3 (Example 1 treatment group), a hole was prepared in the femur with a gauge 23 spinal needle and the composition of Example 1 (50 μL) was injected slowly after removing 50 μL of bone marrow 5 days prior to full-thickness cartilage, and microfracture surgery was performed after the full-thickness cartilage damage.

The microfracture surgery was performed using a thin Kirschner wire with a diameter of 0.2 mm and a depth of 3 mm.

2) Analysis of Cartilage Regeneration Effect

The cartilage regeneration effect of each group was evaluated by visual inspection and microscopy.

The animal models of each group were sacrificed 2 and 4 weeks after the surgery. Immediately after the sacrifice, the knee joint of the rat was exposed by medial approach. After cautiously removing soft tissue such that the cartilage of the knee joint was not damaged, evaluation was made with naked eyes according to the International Cartilage Repair Society (ICRS) guideline. The ICRS guideline evaluates three parameters: (1) degree of defect repair, (2) integration to border zone, and (3) macroscopic appearance. The highest total score was 12 and the lowest score was 0.

The prepared cartilage sample of each group was fixed in 10% neutral formalin for 3 days, decalcified with a decalcifying agent (Calci-Clear Rapid; National Diagnostics, Atlanta, GA, USA) and then prepared into a tissue sample by embedding in paraffin and slicing into 4 mm thickness. For investigation of the presence of glycosaminoglycans, the sample was stained with Safranin O/Fast Green and observed under an optical microscope.

For histochemical assessment of tissue regeneration on the sample surface, the O'Driscoll assessment system and the International Cartilage Repair Society (ICRS) II assessment system were used. The O'Driscoll assessment system systematically evaluates nine parameters: (1) cell morphology, (2) matrix staining, (3) surface regularity, (4) structural integrity, (5) cartilage thickness, (6) bonding to adjacent cartilage, (7) hypocellularity, (8) chondrocyte clustering, and (9) freedom from degenerative changes in adjacent cartilage. The highest total score was 24 and the lowest score was 0.

The ICRS II assessment system systematically evaluates fourteen parameters: (1) tissue morphology, (2) matrix staining, (3) cell morphology, (4) chondrocyte clustering, (5) surface architecture, (6) basal integration, (7) formation of tidemark, (8) subchondral bone abnormalities and marrow fibrosis, (9) inflammation, (10) abnormal calcification (ossification), (11) vascularization, (12) surface/superficial assessment, (13) mid/deep zone assessment, and (14) overall assessment. The highest score for each parameter was 100 and the lowest score was 0. The highest total score was 1400 and the lowest score was 0. The values were represented as mean±SD, and were tested by Mann-Whitney nonparametric multiple comparison test.

3) Analysis Result (Visual Inspection)

Figure 14:
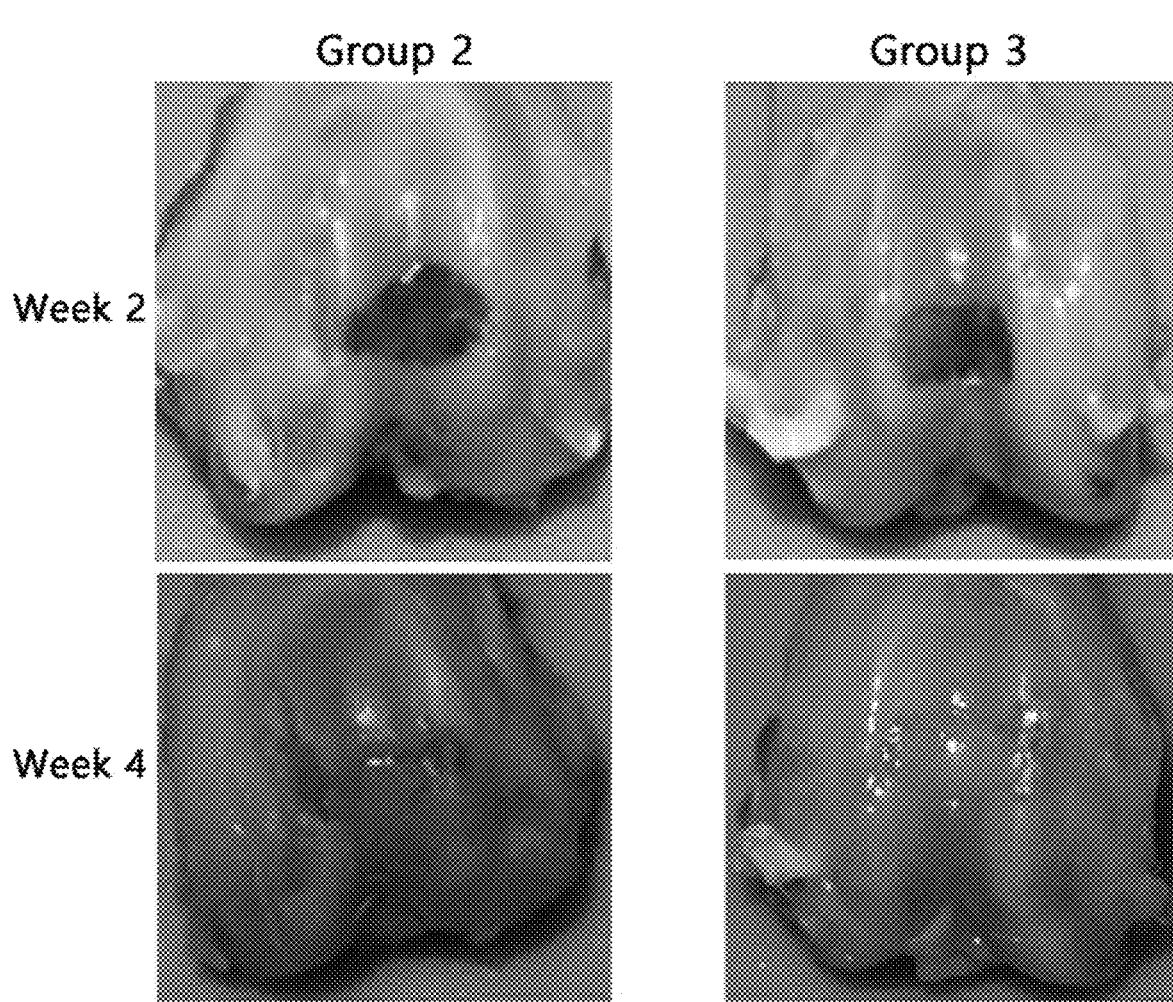
FIG. 14 shows the injured sites of group 2 and group 3 at 2 and 4 weeks after surgery.

FIG. 14 shows the injured sites of group 2 and group 3 at 2 and 4 weeks after surgery. Table 17 shows the result of visual evaluation according to the International Cartilage Repair Society (ICRS) assessment system. The sum of the scores for three parameters was represented as mean±SD (standard deviation). The highest total score was 12 and the lowest score was 0.

TABLE 17

| Visual inspection | Group 1 (damaged group) | Group 2 (microfracture surgery group) | Group 3 (Example 1 composition treatment group) | P value |
|---|---|---|---|---|
| Week 2 | 2.6 ± 1.7 | 4.0 ± 1.6 | 5.0 ± 0.8 | 0.352 |
| Week 4 | 5.2 ± 2.7 | 8.8 ± 1.7 | 9.1 ± 2.2 | 0.574 |

As shown in FIG. 14, regenerating tissues were observed in all the groups as red granulation tissues at 2 weeks after the surgery, and no appreciable difference was observed visually between group 2 and group 3.

At 4 weeks after the surgery, white regenerating tissues were observed at the defective sites of group 2 and group 3. Group 3 showed slightly smoother state and better bonding to the adjacent tissues, but no significant difference could be found with naked eyes.

As shown in Table 17, the score of the assessment according to the International Cartilage Repair Society (ICRS) was 4.0±1.6 for group 2 (microfracture surgery group) and 5.0±0.8 for group 3 (Example 1 composition treatment group) at 2 weeks after the surgery (P=0.352). At 4 weeks after the surgery, the cartilage was regenerated with 8.8±1.7 points for group 2 (microfracture surgery group) and 9.1±2.2 points for group 3 (Example 1 composition treatment group). But, there was no significant difference between the two groups.

4) Analysis Result (O'Driscoll Assessment System)

Figure 15:
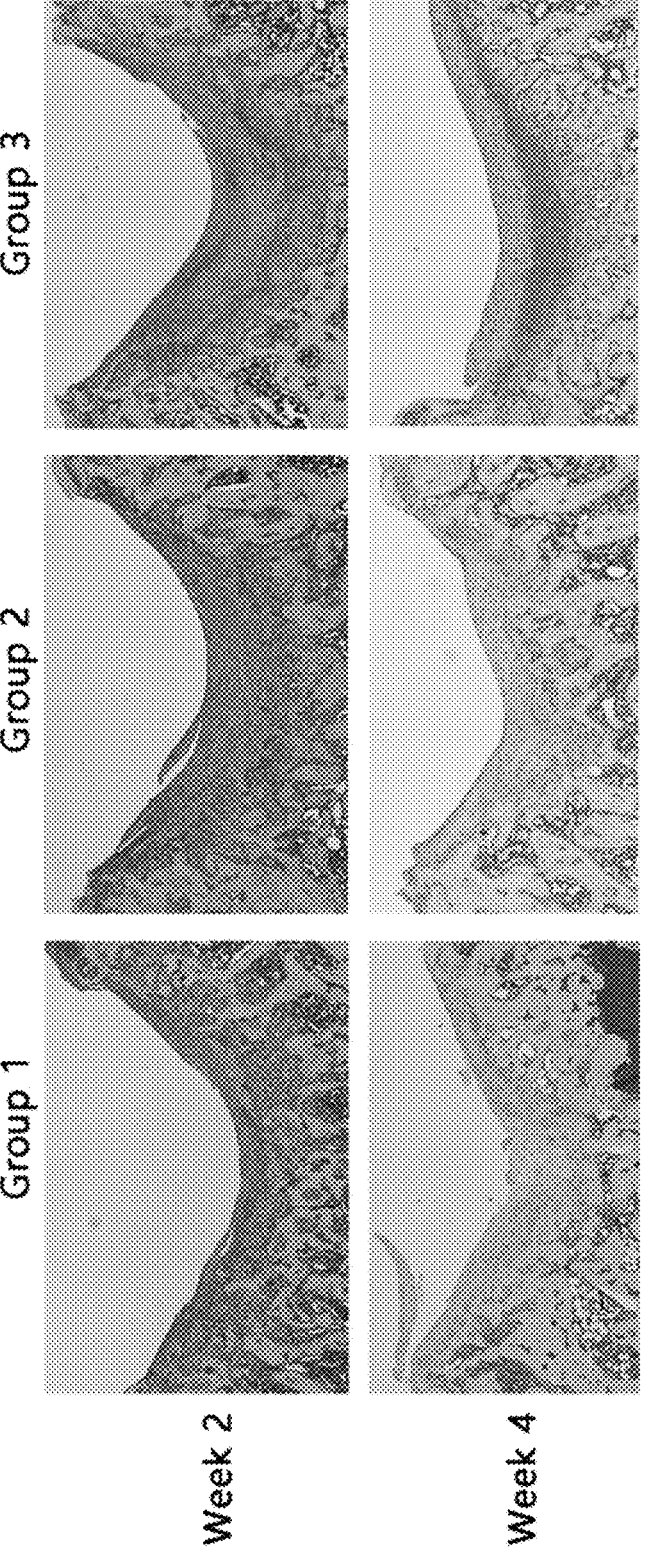
FIG. 15 shows optical microscopic images obtained after staining the surface of tissues acquired from different groups with Safranin O/Fast Green.

FIG. 15 shows optical microscopic images obtained after staining the surface of tissues acquired from different groups with Safranin O/Fast Green. Table 18 shows the result of evaluation according to the O'Driscoll assessment system. The sum of the scores for nine parameters was represented as mean±SD (standard deviation). The highest total score was 24 and the lowest score was 0.

TABLE 18

| O'Driscoll | Group 1 (damaged group) | Group 2 (microfracture surgery group) | Group 3 (Example 1 composition treatment group) | P value |
|---|---|---|---|---|
| Week 2 | 7.9 ± 1.6 | 10.5 ± 2.1 | 14.3 ± 2.9 | 0.114 |
| Week 4 | 11.1 ± 2.7 | 15.1 ± 2.5 | 19.3 ± 2.3 | 0.003 |

As shown in Table 18, the score was 10.5±2.1 for group 2 and 14.3±2.9 for group 3 at 2 weeks after the surgery (P=0.114).

At 4 weeks after the surgery, the score was 15.1±2.5 for group 2 and 19.3±2.3 for group 3. Both groups showed significant improvement with time, and significant difference was observed between group 2 and group 3 (P=0.003).

Group 3 showed significantly higher improvement as compared to group 1 (damaged group) than group 2 (week 2: P=0.035 (group 2), 0.006 (group 3); week 4: P=0.003 (group 2), <0.001 (group 3))

4) Analysis Result (ICRS II Assessment System)

FIG. 15 shows optical microscopic images obtained after staining the surface of tissues acquired from different groups with Safranin O/Fast Green. Table 19 shows the result of evaluation according to the ICRS II assessment system. The sum of the scores for fourteen parameters was represented as mean±SD (standard deviation). The highest total score was 1400 and the lowest score was 0.

TABLE 19

| ICRS II | Group 1 (damaged group) | Group 2 (microfracture surgery group) | Group 3 (Example 1 composition treatment group) | P value |
|---|---|---|---|---|
| Week 2 | 529.3 ± 71.4 | 674.2 ± 151.5 | 888.8 ± 142.2 | 0.067 |
| Week 4 | 860.0 ± 93.1 | 952.5 ± 59.7 | 1103.8 ± 98.6 | 0.001 |

As shown in Table 19, the score was 674.2±151.5 for group 2 and 888.8±142.2 for group 3 at 2 weeks after the surgery (P=0.067).

At 4 weeks after the surgery, the score was 952.5±59.7 for group 2 and 1103.8±98.6 for group 3. Both groups showed significant improvement with time, and significant difference was observed between group 2 and group 3 (P=0.001).

Group 3 showed significantly higher improvement as compared to group 2 (week 4: P=0.020 (group 2), <0.001 (group 3)). In conclusion, although significant difference between the group to which only microfracture surgery was performed (group 2) and the group to which the composition of the present disclosure was treated (group 3) upon visual inspection, it was confirmed that group 3 showed remarkably improved cartilage regeneration upon histochemical assessment.

While the specific exemplary embodiments of the present disclosure have been described in detail, it will be obvious to those having ordinary knowledge in the art that they are merely preferred exemplary embodiments and the scope of the present disclosure is not limited by them. It is to be understood that the substantial scope of the present disclosure is defined by the appended claims and their equivalents.

We claim:

1. A method for increasing proliferation of endogenous stem cells for regenerating torn or ruptured connective tissue, comprising the step of administering a therapeutically effective amount of a pharmaceutical composition to a human or a rat, wherein the pharmaceutical composition comprises platelet-rich plasma (PRP), batroxobin, calcium and tranexamic acid as active ingredients, and wherein the pharmaceutical composition is administered intraosseously.

2. The method according to claim 1, wherein a mixing weight ratio of the platelet-rich plasma (PRP), the batroxobin, the calcium and the tranexamic acid is 10-20: 1-4:1:1-3.

3. The method according to claim 1, wherein the platelet-rich plasma (PRP) is autologous or allogeneic.

4. The method according to claim 1, wherein the concentration of the platelet-rich plasma (PRP) is 200-5,000×10³ platelets/microL.

5. The method according to claim 1, wherein the torn or ruptured connective tissue is torn or ruptured cartilage, torn or ruptured tendon, or torn or ruptured ligament.

6. The method according to claim 1, wherein the pharmaceutical composition increases the proliferation of endogenous cells.

7. The method according to claim 5, wherein the torn or ruptured connective tissue is the torn or ruptured cartilage.

8. The method according to claim 5, wherein the torn or ruptured connective tissue is torn or ruptured tendon.

9. The method according to claim 5, wherein the torn or ruptured connective tissue is torn or ruptured ligament.

10. The method according to claim 1, wherein a volume ratio of platelet-rich plasma (PRP) to the tranexamic acid is from 10:1.15 to 10:1.6.

11. A method for increasing proliferation of endogenous stem cells for regenerating torn or ruptured connective tissue, comprising the step of administering a therapeutically effective amount of a pharmaceutical composition to a human, wherein the pharmaceutical composition comprises platelet-rich plasma (PRP), batroxobin, calcium and tranexamic acid as active ingredients, and wherein the pharmaceutical composition is administered intraosseously.

12. The method of claim 11, wherein a volume ratio of the PRP to the batroxrobin to the calcium to the tranexamic acid is 10:1:0.5:1.15.

\* \* \* \* \*